United States Patent
Cushman et al.

(10) Patent No.: US 8,946,287 B2
(45) Date of Patent: Feb. 3, 2015

(54) CHEMOTHERAPEUTIC FLAVONOIDS, AND SYNTHESES THEREOF

(75) Inventors: Mark S. Cushman, West Lafayette, IN (US); John M. Pezzuto, Hilo, HI (US); Arup Mati, Purga Medinipur (IN)

(73) Assignee: Purdue Research Foundation, West Lafayette, IN (US)

( * ) Notice: Subject to any disclaimer, the term of this patent is extended or adjusted under 35 U.S.C. 154(b) by 860 days.

(21) Appl. No.: 12/519,263

(22) PCT Filed: Dec. 12, 2007

(86) PCT No.: PCT/US2007/087283
§ 371 (c)(1),
(2), (4) Date: Jun. 15, 2009

(87) PCT Pub. No.: WO2008/076767
PCT Pub. Date: Jun. 26, 2008

(65) Prior Publication Data
US 2010/0099755 A1    Apr. 22, 2010

Related U.S. Application Data

(60) Provisional application No. 60/874,550, filed on Dec. 13, 2006.

(51) Int. Cl.
*A01N 43/16*  (2006.01)
*A61K 31/35*  (2006.01)
*C07D 311/00*  (2006.01)
*C07D 311/32*  (2006.01)
*C07D 311/30*  (2006.01)

(52) U.S. Cl.
CPC ............ *C07D 311/32* (2013.01); *C07D 311/30* (2013.01)
USPC .......................................... 514/456; 549/403

(58) Field of Classification Search
USPC .......................................... 514/456; 549/403
See application file for complete search history.

(56) References Cited

U.S. PATENT DOCUMENTS

| | | |
|---|---|---|
| 2003/0125264 A1 | 7/2003 | Malik |
| 2004/0059100 A1 | 3/2004 | Buchholz et al. |
| 2004/0067894 A1* | 4/2004 | Carola et al. ................... 514/27 |

OTHER PUBLICATIONS

Vippagunta et al. Advanced Drug Delivery Reviews, 2001, vol. 48, pp. 3-26.*
Moriyasu et al. J. Nat. Prod., 1998, vol. 61, pp. 185-188.*
Matsuura et al. Biochemical Systematics and Ecology, 1995, vol. 23, No. 5, pp. 539-545.*
Attar, E. and Bulun, S. E. "Aromatase inhibitors: the next generation of therapeutics for endometriosis?," Fertility and Sterility, 2006, pp. 1307-1318.
Bach, T. and Kruger, L., "The preparation of 2,3,5-tri and 2,3-disubstituted furans by regioselective palladium (0)-catalyzed coupling reactions: Application to the syntheses of rosefuran and the F5 furan fatty acid," Eur. J. Org. Chem., 1999, pp. 2045-2057.
Brueggemeier, R. W.; Hackett, J. C. and Diaz-Cruz, E. S., "Aromatase inhibitors in the treatment of breast cancer," Endocrine Rev., 2005, vol. 26, pp. 331-345.
Decensi, A.; Serrano, D.; Bonanni, B.; Cazzaniga, M.; Guerrieri-Gonzaga, A., "Breast Cancer Prevention Trials Using Retinoids," J. Mammary Gland Biol. Neoplasia, 2003, vol. 8, pp. 19-30.
Freireich, E.J.; Gehan, E. A.; Rall D. P.; Schmidt, L. H.; Skipper, H. E., "Quantitative Comparison of Toxicity of Anticancer Agents in Mouse, Rat, Hamster, Dog, Monkey and Man," Cancer Chemother. Rep., 1966, vol. 50, No. 4, pp. 219-244.
Geisler, J. and Lonning, P. E., "Aromatase inhibition: Translation into a successful therapeutic approach," Clin. Cancer Res., 2005, vol. 11, pp. 2809-2821.
Gerhauser, C.; Mar, W.; Lee, S. K.; Suh, N.; Luo, Y.; Kosmeder, J.; Luyengi, L.; Fong, H. H. S.; Kinghorn, A. D.; Moriarty, R. M.; Mehta, R. G.; Constantinou, A.; Moon, R. C.; Pezzuto, J. M., "Rotenoids Mediate Potent Cancer Chemopreventive Activity through Transcriptional Regulation of Ornithine Decarboxylase," Nature Med., 1995, vol. 1, pp. 260-266.
Glusenkamp, K-H. and Buchi, G., "C-prenylation of phenols promoted by aluminium oxide surfaces," J. Org. Chem., 1986, vol. 51. pp. 4481-4483.
Henderson, D.; Habenicht, U.-F.; Nishino, Y. and El Etreby, M. F., "Estrogens and benign prostatic hyperplasia: the basis for aromatase inhibitor therapy," Steroids, 1987, vol. 50, pp. 219-233.
Homhual, S.; Zhang, H. J.; Bunyapraphatsara, N.; Kondratyuk, T. P.; Santarsiero, B. D.; Mesecar, A. D.; Herunsalee, A.; Chaukul, W.; Pezzuto, J. M.; Fong, H. H. S., "Bruguiesulfurol, a New Sulfur Compound from *Bruguiera gymnorrhiza*," Planta Med., 2006, vol. 72, pp. 255-260.
Hong, W. K.; Sporn, M. B., "Recent Advances in Chemoprevention of Cancer," Science, 1997, vol. 278, pp. 1073-1077.
Howell, A.; Robertson, J. F. R.; Vergote, I., "A review of the efficacy of anastrozole in postmenopausal women with advanced breast cancer with visceral metastases," Breast Cancer Res. Treat., 2003, vol. 82, pp. 215-222.
Jain, A. C. and Prasad, A. K., "Synthesis of amorilin (euchrenone a3) and 5,7-dihydroxy-6",6"-dimethyl-6,8-di-C-prenylpyrano[2",3",4',3']flavanone," Indian. J. Chem., 1990, vol. 29B, pp. 525-528.
Karr, J. P.; Kaburagi, Y.; Mann, C. F. and Sandberg, A. A., "The potential significance of aromatase in the etiology and treatment of prostatic disease," Steroids, 1987, vol. 50, pp. 449-457.

(Continued)

*Primary Examiner* — Samira Jean-Louis
(74) *Attorney, Agent, or Firm* — Mark S. Cohen; Pearl Cohen Zedek Latzer Baratz LLP

(57) ABSTRACT

Substituted flavonoid compounds, and pharmaceutical formulations of flavonoid compounds are described. Also described are processes for preparing flavonid compounds, as are methods for treating cancer in mammals using the described flavonoid compounds or pharmaceutical formulations thereof.

10 Claims, 12 Drawing Sheets

(56) References Cited

OTHER PUBLICATIONS

Kelloff, G. J.; Lubet, R. A.; Lieberman, R.; Eisenhauer, K.; Steele, V. E.; Crowell, J. A.; Hawk, E. T.; Boone, C. W. and Sigman, C. C., "Aromatase inhibitors as potential cancer chemopreventives," Cancer Epidemiol. Biomark. Prev., 1998, vol. 7, pp. 65-78.

Knolker, H.-J.; Baum, E.; Reddy, K. R., "Transition metal complexes in organic synthesis. Part 58: First enantioselective total synthesis of the potent neuronal cell protecting substance carquionstatin A from (R)-propene oxide," Tetrahedron Lett., 2000, vol. 41, pp. 1171-1174.

Kyogoku, K. K.; Hatayama, K.; Yokomori, S.; Seki, T. and Tanaka, I., "Synthesis of Isoprenyl chalcone "sophoradin" Isolated from sophora subprostrata," Agric. Biol. Chem., 1975, vol. 1, pp. 133-138.

Lee, D.; Bhat, K. P. L.; Fong, H. H. S.; Farnsworth, N. R.; Pezzuto, J. M. and Kinghorn, A. D., "Aromatase inhibitors from *Broussonetia papyrifera*," J. Nat. Prod., 2001, vol. 64, pp. 1286-1293.

Lonning, P. E.; Bajetta, E.; Murray, R.; Tubiana-Hulin, M.; Eisenberg, P. D.; Mickiewicz, E.; Celio, L.; Pitt, P.; Mita, M.; Aaronson, N. K.; Fowst, C.; Arkhipov, A.; Salle, E-d.; Polli, A. and Massimini, G., "Activity of Exemestane in Metastatic Breast Cancer After Failure of Nonsteroidal Aromatase Inhibitors: A Phase II Trial," J. Clin. Oncol., 2000, vol. 18, pp. 2234-2244.

Mata-Greenwood, E.; Ito, A.; Westenburg, H.; Cui, B.; Mehta, R. G.; Kinghorn, A. D.; Pezzuto, J. M., "Discovery of Novel Inducers of Cellular Differentiation Using HL-60 Promyelocytic Cells," Anticancer Res., 2001, vol. 21, pp. 1763-1770.

Michaud, L. B., "Adjuvant use of aromatase inhibitors in postmenopausal women with breast cancer," Am. J. Health-Syst. Pharm, 2005, vol. 62, pp. 266-273.

Miller, W. R., "Aromatase inhibitors: mechanism of action and role in the treatment of breast cancer," Semin. Oncol., 2003, vol. 30, pp. 3-11.

Odejinmi, S. I. and Wiemer, D. F., "Application of benzyl protecting groups in the synthesis of prenylated aromatic compounds," Tetrahedron Lett., 2005, vol. 46, pp. 3871-3874.

Pezzuto, J. M.; Kosmeder, J. W.; Park, E. J.; Lee, S. K.; Cuendet, M.; Gills, J.; Bhat, K.; Grubjesic, S.; Park, H. S.; Mata-Greenwood, E.; Tan, Y.; Yu, R.; Lantvit, D. D.; Kinghorn, A. D., "Characterization of Natural Product Chemopreventive Agents," Humana Press, Inc., Totowa, NJ, 2005: vol. 2, pp. 3-37.

Recanatini, M.; Cavalli, A. and Valenti, P., "Nonsteroidal aromatase inhibitors: recent advances," Med. Res. Rev, 2002, vol. 22, pp. 282-304.

Reddy, P. "A review of the newer aromatase inhibitors in the management of metastatic breast cancer," J. Clin. Pharmacol. Ther., 1998, vol. 23, pp. 81-90.

Scientific Tables, Geigy Pharmaceuticals, Ardsley, New York, 1970, pp. 537-538.

Scott, L. J. and Keam, S. J., "Letrozole: In postmenopausal hormone-responsive early-stage breast cancer," Drugs, 2006, vol. 66, pp. 353-362.

Suh, N.; Luyengi, L.; Fong, H. H. S.; Kinghorn, A. D.; Pezzuto, J. M., "Discovery of Natural Product Chemopreventive Agents Utilizing HL-60 Cell Differentiation as a Model," Anticancer Res., 1995, vol. 15, pp. 233-240.

Tobias, J. S., "Endocrine approaches for the treatment of early and advanced breast cancer in postmenopausal women," Int. J. Biochem. Cell Biol., 2004, vol. 36, pp. 2112-2119.

Trayner, I. D.; Bustorff, T.; Etches, A. E.; Mufti, G. J.; Foss, Y.; Farzaneh, F., "Changes in Antigen Expression on Differentiating HL60 Cells treated with Dimethylsulphoxide, all-trans Retinoic Acid, $\alpha 1,25$-Dihydroxyvitamin $D_3$ or 12-O-Tetradecanoyl phorbol-13-acetate," Leuk. Res., 1998, vol. 22, pp. 537-547.

Tucker, C. E.; Majid, T. N.; Knochel, P., "Preparation of Highly Functionalized Magnesium, Zinc, and Copper Aryl and Alkenyl Organometallics via the Corresponding Organolithiums," J. Am. Chem. Soc., 1992, vol. 114, pp. 3983-3985.

Varmus, H., "The New Era in Cancer Research," Science, 2006, vol. 312, pp. 1162-1165.

Vogel, C. L., "Hormonal approaches to breast cancer treatment and prevention: an overview," Semin. Oncol., 1996, vol. 23, pp. 2-9.

Wollenweber, E.; Iinuma, M.; Tanaka, T.; Mizuno, M., "5-Hydroxy-6,2'-dimethoxyflavone from *Primula denticulata*," Phytochemistry, 1990, vol. 29, pp. 633-637.

PCT International Search Report for PCT/US2007/087283 completed by the US Searching Authority on Mar. 19, 2008.

Hu et al. "Synthesis and Fungicidal Activity of Flavanone Derivatives Containing Isopentenyl Group," Chinese Journal of Applied Science, vol. 20, No. 2, Dec. 2003, 1 page, Abstract.

Hu et al. "Synthesis and Fungicidal Activity of Flavanone Derivatives Containing Isopentenyl Group," Chinese Journal of Applied Science, vol. 20, No. 2, Dec. 2003, 5 pages, partial translation.

\* cited by examiner

US 8,946,287 B2

CHEMOTHERAPEUTIC FLAVONOIDS, AND SYNTHESES THEREOF

CROSS REFERENCE TO RELATED APPLICATIONS

This application is a U.S. national counterpart application of international application serial No. PCT/US2007/087283 filed Dec. 12, 2007, which claims priority to U.S. Provisional Patent Application No. 60/874,550 filed Dec. 13, 2006. The entire disclosures of PCT/US2007/087283 and U.S. Ser. No. 60/874,550 are hereby incorporated by reference.

GOVERNMENT RIGHTS

This invention was made with government support Grant No. P01 CA048112 awarded by the National Institutes of Health/National Cancer Institute. The United States Government has certain rights in this invention.

TECHNICAL FIELD

The invention described herein pertains to substituted flavonoid compounds. The invention described herein also pertains to methods for treating cancer in mammals using flavonoid compounds.

BACKGROUND

The control and cure of cancer represents one of our most challenging health problems. Cancer is currently the second most common cause of death in the United States, and it is likely to become the most common cause in the near future. See, Varmus, H. The New Era in Cancer Research. *Science*, 2006, 312, 1162-1165. Breast cancer, the second leading cause of cancer deaths, is the most common cancer among postmenopausal women. According to the World Health Organization, more than 1.2 million people will be diagnosed with breast cancer this year worldwide, including more than 0.2 million victims in the United States. See, American Cancer Society web site. Available at: http://www.cancer.org Accessed on Aug. 18, 2006.

Chemoprevention is the use of either synthetic drugs or natural products to inhibit, reverse, or suppress the development of invasive malignant cancer, either by blocking the DNA damage that initiates carcinogenesis or by arresting or reversing the progression of premalignant cells in which DNA damage has already started. Chemoprevention is one of the most direct ways to reduce cancer-related morbidity and mortality. See, Hong, W. K.; Sporn, M. B. Recent Advances in Chemoprevention of Cancer. *Science* 1997, 278, 1073-1077.

The role of estrogens in the development of breast cancer is well established with the majority of postmenopausal women having hormone receptor-positive tumors. See, Vogel, C. L. Hormonal approaches to breast cancer treatment and prevention: an overview. *Semin. Oncol.* 1996, 23, 2-9; Reddy, P. A review of the newer aromatase inhibitors in the management of metastatic breast cancer. *J. Clin. Pharmacol. Ther.* 1998, 23, 81-90.; Tobias, J. S. Endocrine approaches for the treatment of early and advanced breast cancer in postmenopausal women. *Int. J. Biochem. Cell Biol.* 2004, 36, 2112-2119. One chemopreventive strategy for breast cancers is to decrease estrogen production. See, Karr, J. P.; Kaburagi, Y.; Mann, C. F. and Sandberg, A. A. The potential significance of aromatase in the etiology and treatment of prostatic disease. *Steroids*, 1987, 50, 449-457; Henderson, D.; Habenicht, U.-F.; Nishino, Y. and el Etreby, M. F. Estrogens and benign prostatic hyperplasia: the basis for aromatase inhibitor therapy. *Steroids*, 1987, 50, 219-233. Aromatase, a key cytochrome P450 enzyme, catalyzes the rate-limiting aromatization step for the conversion of androgens (testosterone and androstenedione) to estrogens (estradiol and estrone) and this pathway is the only source for estrogen in postmenopausal women. Because estrogen production is the last step in the biosynthetic sequence of steroid production, selective inhibition of aromatase would not be expected to interfere with the production of other useful steroids, such as adrenal corticoids. Thus, aromatase inhibitors have become attractive chemopreventive agents in the treatment of estrogen-dependent breast cancers. See, Attar, E. and Bulun, S. E. Aromatase inhibitors: the next generation of therapeutics for endometriosis. *Fertility and Sterility*, 2006, 1307-1318; Geisler, J. and Lonning, E. Aromatase inhibition: Translation into successful therapeutic approach. *Clin. Cancer Res.* 2005, 11, 2809-2821; Michaud, L. B., Adjuvant use of aromatase inhibitors in postmenopausal women with breast cancer. *Am. J. Health-syst. Pharm*, 2005, 62, 266-273; Brueggemeier, R. W.; Hackett, J. C. and Diaz-Cruz, E. S. Aromatase inhibitors in the treatment of breast cancer. *Endocrine Rev.* 2005, 26, 331-345; Miller, W. R. Aromatase inhibitors: mechanism of action and role in the treatment of breast cancer. *Semin. Oncol.* 2003, 30, 3-11; Recanatini, M.; Cavalli, A. and Valenti, P. Nonsteroidal aromatase inhibitors: recent advances. *Med. Res. Rev.* 2002, 22, 282-304; Kelloff, G. J.; lubet, R. A.; Lieberman, R.; Eisenhauer, K.; Steele, V. E.; Crowell, J. A.; Hawk, E. T.; Boone, C. W. and Sigman, C. C. Aromatase inhibitors as potential cancer chemopreventives. *Cancer Epidemiol. Biomark. Prev.* 1998, 7, 65, the disclosures of which are incorporated herein by reference.

In the last two decades, several classes of steroidal and nonsteroidal synthetic aromatase inhibitors such as aminogulethimide and imidazole or triazole derivatives have been designed. The first FDA-approved aromatase inhibitor, aminogluthethimide, has shown some clinical benefit in breast cancer trials, but lack of selectivity and its weak aromatase inhibitory activity has limited its usefulness. Other aromatase inhibitors recently approved by the FDA include the nonsteroidals anastrazole and letrozole, as well as the steroidal exemestane that, like all aromatase inhibitors, inhibit the synthesis of estrogen in tissues other than the ovaries and also cause several severe adverse effects. See, Howell, A.; Robertson, J. F. R.; Vergote, I. A review of the efficacy of anastrozole in postmenopausal women with advanced breast cancer with visceral metastases. Breast Cancer Res. Treat. 2003, 82, 215; Scott J. Lesley and Keam J. Susan. Letrozole: In postmenopausal hormone-responsive early-stage breast cancer. *Drugs* 2006, 66, 353-362; Lonning, B. P. E.; Bajetta, E.; Murray, R.; Tubiana-Hulin, M.; Eisenberg, P. D.; Mickiewicz, E.; Celio, L.; Pitt, P.; Mita, M.; Aaronson, N. K.; Fowst, C.; Arkhipov, A.; Salle, E-d.; Polli, A. and Massimini, G. Activity of Exemestane in Metastatic Breast Cancer After Failure of Nonsteroidal Aromatase Inhibitors: A Phase II Trial. *J. Clin. Oncol.* 2000, 18, 2234-2244, the disclosures of which are incorporated herein by reference.

Besides the development of synthetic aromatase inhibitors, there is a continuing search for new classes of natural products to inhibit aromatase in order to discover novel breast cancer chemopreventive agents. In this regard, abyssinone II (7-hydroxy-2-(4-hydroxy-3-(3-methylbut-2-enyl)phenyl) chroman-4-one), a prenylated flavanone isolated from the Chinese medicinal plant *Broussonetia papyafera*, has shown significant inhibitory activity as its (2S) enantiomer in an aromatase assay with an $IC_{50}$ of 0.37 μM observed in a radiometric method. See, Lee, D. P.; Bhat, L.; Fong, H. H. S.; Farnsworth, N. R.; Pezzuto, J. M. and Kinghorn, A. D. Aromatase inhibitors from *Broussonetia papyrifera. J. Nat. Prod.* 2001, 64, 1286-1293, the disclosure of which is incorporated herein by reference. Abyssinone II, therefore, has the potential to inhibit carcinogenesis, and was selected as one of the chemopreventive agents for further studies under the Rapid Access to Preventive Intervention Development (RAPID) program of the National Cancer Institute.

Several food-based chemopreventive agents have also shown promise in clinical trials. See, Decensi, A.; Serrano, D.; Bonanni, B.; Cazzaniga, M.; Guerrieri-Gonzales, A. Breast Cancer Prevention Trials Using Retinoids. *J. Mammary Gland Biol. Neoplasia* 2003, 8, 19-30. The medicinal value of zapote blanco, a fruit of *Casimiroa edulis* Llave & Lex (Rutaceae) that is consumed in many parts of the world, was first discovered by the Aztecs, and crude plant extracts of the seeds or leaves of *Casimiroa edulis* have been found to affect blood pressure, cardiac activity, aortic muscular tone, and to possess anticonvulsant activity. Recently, zapotin (5,6,2',6'-tetramethoxyflavone), a polymethoxylated flavonoid isolated from zapote blanco seeds, was found to be a non-toxic inducer of cellular differentiation with cultured HL-60 promyelocytic cells. See, Mata-Greenwood, E.; Ito, A.; Westenburg, H.; Cui, B.; Mehta, R. G.; Kinghorn, A. D.; Pezzuto, J. M. Discovery of Novel Inducers of Cellular Differentiation Using HL-60 Promyelocytic Cells. *Anticancer Res.* 2001, 21, 1763-1770, the disclosure of which is incorporated herein by reference. Zapotin, therefore, has the potential to inhibit carcinogenesis.

The discovery of compounds specifically targeting cancer cells, or the cellular mechanisms involved in the proliferation of cancer cells, can provide significant advancement in the eradication and/or control of cancer. The limited availability of abyssinone II and zapotin from natural sources as well as from poor-yielding syntheses has hampered not only more advanced biological testing of these flavonoid compounds, but also the syntheses of various analogues the testing of which could elucidate structure-activity relationships and guide further investigation and development of new chemopreventive agents. Therefore, the development of practical syntheses of abyssinone II and zapotin would permit a more thorough evaluation of their potential as chemopreventive agents, and establish the basis for respective analogue programs.

SUMMARY OF THE INVENTION

Described herein are substituted flavonoid compounds, and more specifically, racemic abyssinone II, zapotin, and analogues thereof. The flavonoid compounds described herein may be useful for treating cancer. Also described herein are pharmaceutical compositions of such compounds, processes for preparing and testing such compounds, and methods for treating cancer by administering therapeutically effective amounts of substituted flavonoid compounds alone or as pharmaceutical compositions.

In one illustrative embodiment, compounds of formula I are described

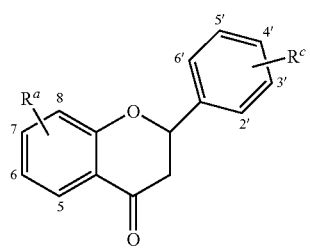

(I)

and pharmaceutically acceptable salts, hydrates, and solvates thereof, wherein:

$R^a$ and $R^c$ each independently represent hydrogen, or one or more optional and independently selected monovalent and divalent substituents.

In one aspect, $R^a$ represents 1-4 substituents each of which is independently selected from the group consisting of halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof; or $R^a$ represents 2-4 substituents where 2 of said substituents are adjacent substituents and are taken together with the attached carbons to form an optionally substituted heterocycle, and where the remaining substituents, in cases where $R^a$ represents 3-4 substituents, are each independently selected from the group consisting of halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof.

In another aspect, $R^c$ represents 1-4 substituents each of which is independently selected from the group consisting of halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof; or $R^c$ represents 2-4 substituents where 2 of said substituents are adjacent substituents and are taken together with the attached carbons to form an optionally substituted heterocycle, and where the remaining substituents, in cases where $R^a$ represents 3-4 substituents, are each independently selected from the group consisting of halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof.

In another illustrative embodiment, compounds of formula I are described wherein $R^a$ represents 1-4 substituents each of which is independently selected from the group consisting of halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof.

In another illustrative embodiment, compounds of formula I are described wherein $R^a$ represents 2-4 substituents where 2 of said substituents are adjacent substituents and are taken together with the attached carbons to form an optionally substituted heterocycle, and where any remaining substituents are each independently selected from the group consisting of halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof.

In another illustrative embodiment, compounds of formula I are described wherein $R^c$ represents 1-4 substituents each of which is independently selected from the group consisting of halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof.

In another illustrative embodiment, compounds of formula I are described wherein $R^c$ represents 2-4 substituents where 2 of said substituents are adjacent substituents and are taken together with the attached carbons to form an optionally substituted heterocycle, and where any remaining substituents are each independently selected from the group consisting of halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof.

In another illustrative embodiment, compounds of formula I are described wherein when $R^a$ is 7-hydroxy, $R^c$ is not 4-hydroxy-3-(3-methylbut-2-enyl).

In another illustrative embodiment, compounds of formula I are described wherein when $R^a$ comprises 7-hydroxy, $R^c$ does not comprise 4'-hydroxy.

In another illustrative embodiment, compounds of formula I are described wherein $R^a$ includes at least one substituent selected from the group consisting of 7-hydroxy, 7-methoxy, 7-alkoxy and 7-substituted alkoxy; and $R^c$ is one or more alkoxy groups.

In another illustrative embodiment, compounds of formula II are described

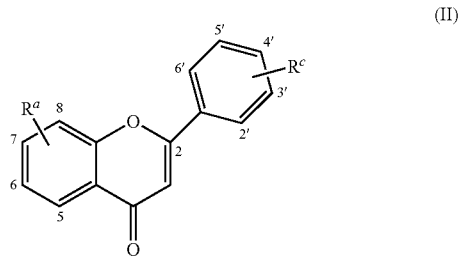

and pharmaceutically acceptable salts, hydrates, and solvates thereof, wherein:

$R^a$ and $R^c$ each independently represent hydrogen, or one or more optional and independently selected monovalent and divalent substituents.

In one aspect, $R^a$ represents 1-4 substituents each of which is independently selected from the group consisting of halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof; or $R^a$ represents 2-4 substituents where 2 of said substituents are adjacent substituents and are taken together with the attached carbons to form an optionally substituted heterocycle, and where the remaining substituents, in cases where $R^a$ represents 3-4 substituents, are each independently selected from the group consisting of halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof.

In another aspect, $R^c$ represents 1-4 substituents each of which is independently selected from the group consisting of halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof; or $R^c$ represents 2-4 substituents where 2 of said substituents are adjacent substituents and are taken together with the attached carbons to form an optionally substituted heterocycle, and where the remaining substituents, in cases where $R^c$ represents 3-4 substituents, are each independently selected from the group consisting of halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof.

In another illustrative embodiment, compounds of formula II are described wherein $R^a$ represents 1-4 substituents each of which is independently selected from the group consisting of halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof.

In another illustrative embodiment, compounds of formula II are described wherein $R^a$ represents 2-4 substituents where 2 of said substituents are adjacent substituents and are taken together with the attached carbons to form an optionally substituted heterocycle, and where any remaining substituents are each independently selected from the group consisting of halo, hydroxy, optionally substituted alkyl, optionally substituted alkenyl, optionally substituted alkoxy, cyano, intro, optionally substituted alkylthio, optionally substituted alkylsulfonyl, carboxylic acid and derivatives thereof, and sulfonic acid and derivatives thereof.

In another illustrative embodiment, compounds of formula II are described wherein $R^c$ represents 1-4 substituents each of which is independently selected from the group consisting of halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof.

In another illustrative embodiment, compounds of formula II are described wherein $R^c$ represents 2-4 substituents where 2 of said substituents are adjacent substituents and are taken together with the attached carbons to form an optionally substituted heterocycle, and where any remaining substituents are each independently selected from the group consisting of halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof.

In another illustrative embodiment, compounds of formula II are described wherein when $R^a$ is 5,6-dimethoxy, $R^c$ is not 2',6'-dimethoxy.

In another illustrative embodiment, compounds of formula II are described wherein when $R^a$ COMPRISES 5,6-dimethoxy, $R^c$ DOES not COMPRISE 2'-METHOXY In another illustrative embodiment, flavonoid compounds of formulae I and II described herein are useful for treating cancer or tumors. In one aspect, compounds of formula I described herein display inhibitory activity in an aromatase assay. In another aspect, flavonoid compounds of formulae I and II described herein may be efficacious against various types of human cancers. In yet another aspect, flavonoid compounds of formulae I and II described herein may be chemically more stable than abyssinone II and zapotin, respectively. In still another aspect, flavonoid compounds of formula II described herein exhibit activity as a non-toxic inducer of cellular differentiation with cultured HL-60 promyelocytic cells.

In another illustrative embodiment, methods for treating human cancers are described. In one aspect of the methods described herein, the cancers are attributable to abnormally fast cell growth, reproduction, and/or proliferation. In another aspect, the cancers treatable by compounds of formula I are responsive to enzyme inhibition, such as inhibition of aromatase. In another aspect, the cancers treatable by compounds of formula II are responsive to an inducer of cellular differentiation.

In another illustrative embodiment, processes are described herein for preparing flavonoid compounds of formula I comprising the steps of preparing and reacting an appropriately substituted o-hydroxyacetophenone and an appropriately substituted benzaldehyde of respective formulae

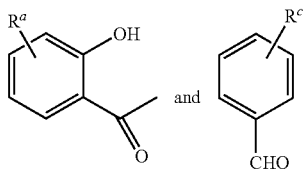

under Claisen-Schmidt conditions to provide an intermediate enone of the formula

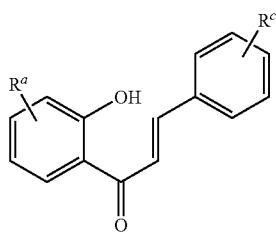

and subsequently conducting isomeric cyclization with sodium acetate in refluxing ethanol, wherein $R^a$ and $R^c$ are as defined herein for compounds of formula I. It is appreciated that other bases and other solvents, including alcohol solvents may be used in this illustrative process.

In another illustrative embodiment, processes for preparing flavonoid compounds of formula II are described. In one embodiment, the processes include preparing an intermediate dilithium dianion of the formula

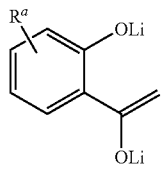

where the process comprises preparing an appropriately substituted o-hydroxyacetophenone for reaction with lithium hexamethyldisilylazide in tetrahydrofuran, followed by direct regioselective acylation at carbon with an appropriately substituted benzoyl chloride to produce an intermediate β-diketone of the formula

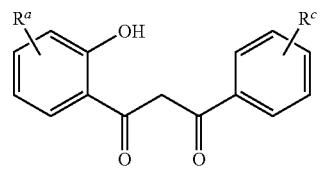

with subsequent cyclization under acidic conditions at elevated temperature, wherein $R^a$ and $R^c$ are as defined herein for compounds of formula II. It is appreciated that other dimetallo dianions formed from appropriate bases may be used in this illustrative process. It is further appreciated that other solvents, including but not limited to ether, DME, NMP, and the like may be used in this illustrative process. It is further appreciated that other activating groups in addition to acyl chlorides may be used in this illustrative process.

It is to be understood that each of the aspects of the various illustrative embodiments described herein may be modified and/or combined as additional illustrative embodiments.

BRIEF DESCRIPTION OF THE DRAWINGS

Additional illustrative embodiments are described with reference to the following figures.

Cells were treated with DMSO (A), 0.75 μM (B), 1.5 μM (C), 3 μM (D), 6 μM (E), or 12 μM (F) of zapotin (15), and harvested for cell cycle analysis 24 h later. For 30 min prior to harvest, cells synthesizing DNA were allowed to incorporate BrdU. Cells synthesizing DNA during this period were then labeled using fluorescein-modified antibody to BrdU and were analyzed by flow cytometry.

Figure 6:
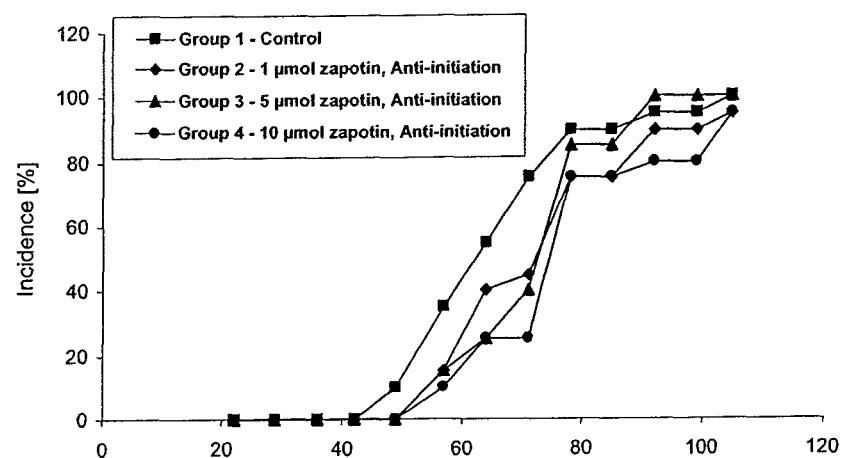

FIG. 6. Effects of zapotin (15) administration using an anti-initiation protocol on tumor incidence in female CD-1 mice in a TPA-dependent, DMBA induced, two-stage mouse skin carcinogenesis model.

Figure 7:
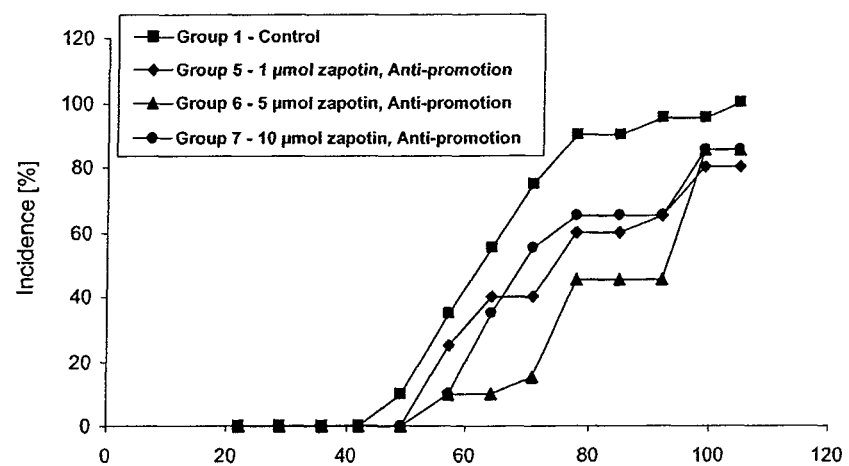

FIG. 7. Effects of zapotin (15) administration using an anti-promotion protocol on tumor incidence in female CD-1 mice in a TPA-dependent, DMBA induced, two-stage mouse skin carcinogenesis model.

Figure 8:
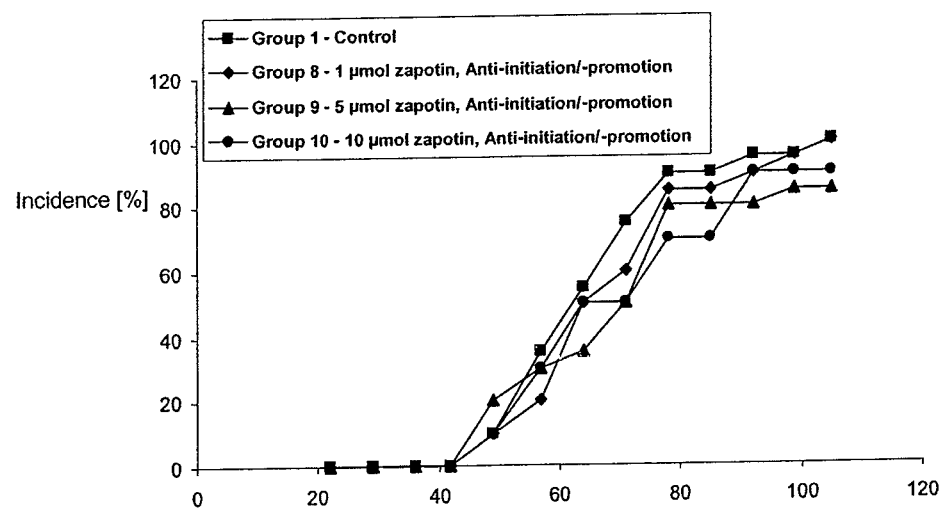

FIG. 8. Effects of zapotin (15) administration using an anti-initiation/promotion protocol on tumor incidence in female CD-1 mice in a TPA-dependent, DMBA induced, two-stage mouse skin carcinogenesis model.

Figure 9:
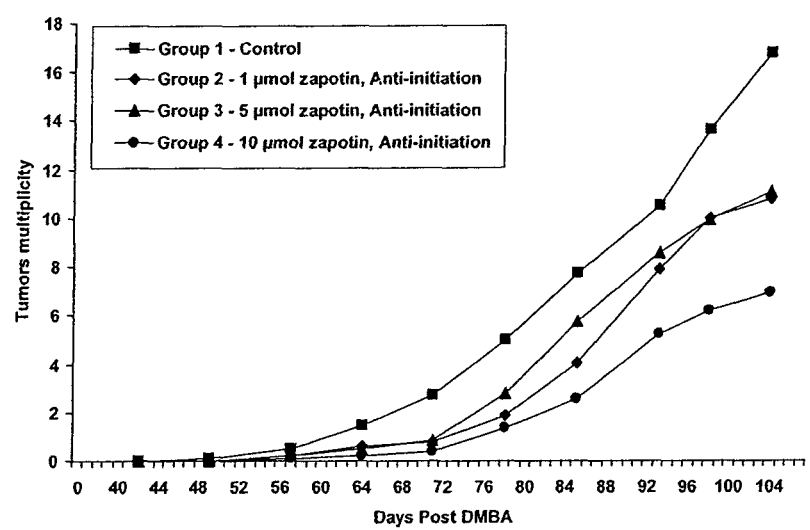

FIG. 9. Effects of zapotin (15) administration using an anti-initiation protocol on tumor multiplicity in female CD-1 mice in a TPA-dependent, DMBA induced, two-stage mouse skin carcinogenesis model.

Figure 10:
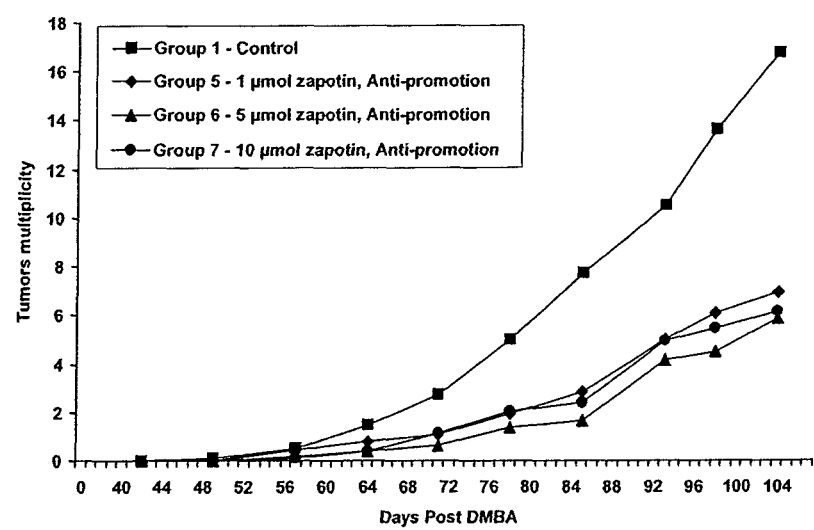

FIG. 10. Effects of zapotin (15) administration using an anti-promotion protocol on tumor multiplicity in female CD-1 mice in a TPA-dependent, DMBA induced, two-stage mouse skin carcinogenesis model.

Figure 11:
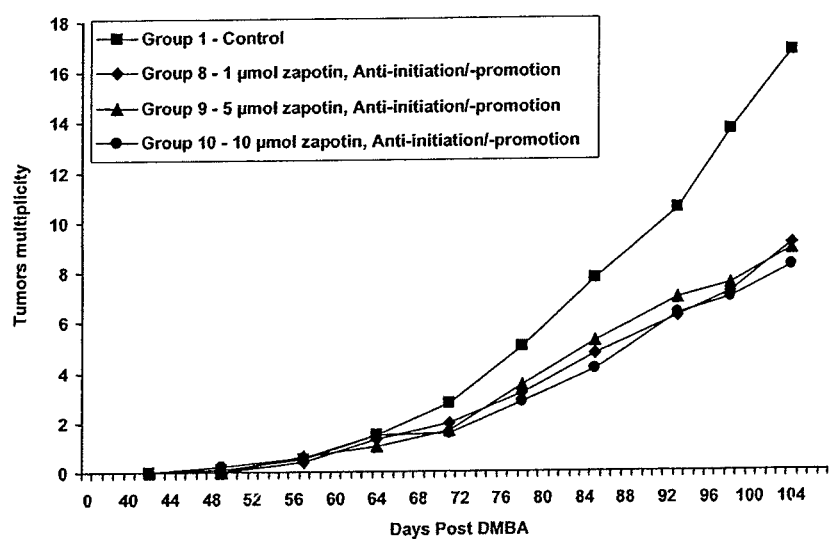

FIG. 11. Effects of zapotin (15) administration using an anti-initiation/promotion protocol on tumor multiplicity in female CD-1 mice in a TPA-dependent, DMBA induced, two-stage mouse skin carcinogenesis model.

Figure 12:
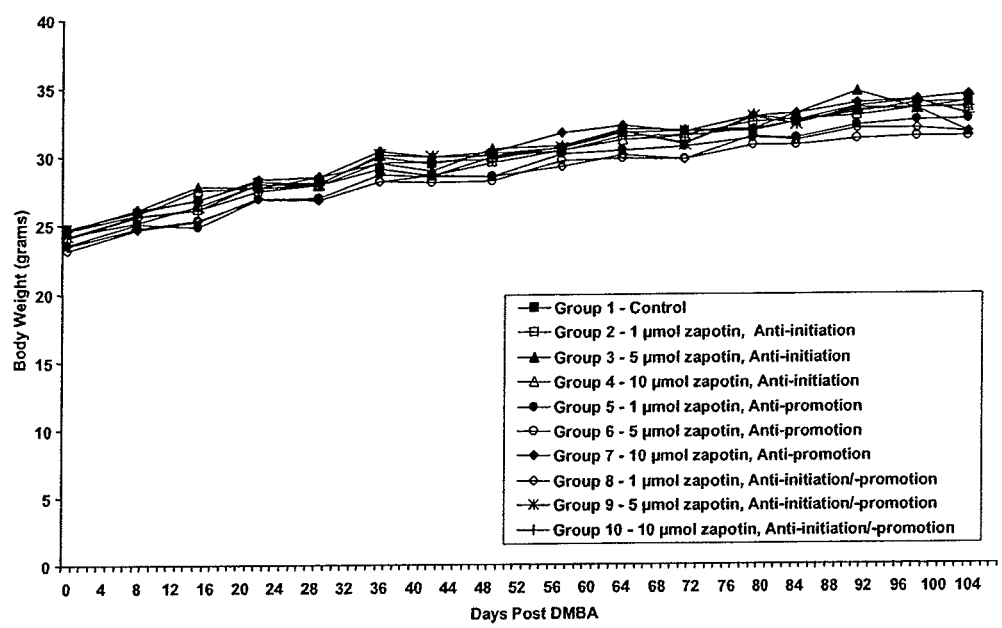

FIG. 12. Effects of zapotin (15) administration on the body weight of female CD-1 mice in the TPA-dependent, DMBA induced, two-stage mouse skin carcinogenesis model using an anti-initiation protocol, an anti-promotion protocol or an anti-initiation/promotion protocol.

DETAILED DESCRIPTION

In one illustrative embodiment, compounds of formula I are described

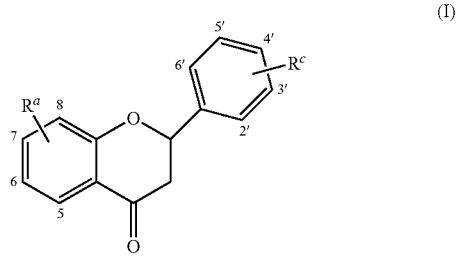

and pharmaceutically acceptable salts, hydrates, and solvates thereof, wherein:

$R^a$ represents 1-4 substituents each of which is independently selected from the group consisting of hydrogen, halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof; or $R^a$ represents 2-4 substituents where 2 of said substituents are adjacent substituents and are taken together with the attached carbons to form an optionally substituted heterocycle, and where the remaining substituents, in cases where $R^a$ represents 3-4 substituents, are each independently selected from the group consisting of hydrogen, halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof; and $R^c$ represents 1-4 substituents each of which is independently selected from the group consisting of hydrogen, halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof, or $R^c$ represents 2-4 substituents where 2 of said substituents are adjacent substituents and are taken together with the attached carbons to form an optionally substituted heterocycle, and where the remaining substituents, in cases where $R^c$ represents 3-4 substituents, are each independently selected from the group consisting of hydrogen, halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof.

As used herein, the term "alkyl" refers to a saturated monovalent chain of carbon atoms, which may be optionally branched. It is understood that in embodiments that include alkyl, illustrative variations of those embodiments include lower alkyl, such as $C_1$-$C_6$, $C_1$-$C_4$ alkyl, methyl, ethyl, propyl, 3-methylpentyl, and the like.

As used herein, the term "alkenyl" refers to an unsaturated monovalent chain of carbon atoms including at least one double bond, which may be optionally branched. It is understood that in embodiments that include alkenyl, illustrative variations of those embodiments include lower alkenyl, such as $C_2$-$C_6$, $C_2$-$C_4$ alkenyl, for example, 3-methylbut-2-enyl.

As used herein, the term "alkylene" refers to a saturated bivalent chain of carbon atoms, which may be optionally branched. It is understood that in embodiments that include alkylene, illustrative variations of those embodiments include lower alkylene, such as $C_2$-$C_4$ alkylene, methylene, ethylene, propylene, 3-methylpentylene, and the like.

As used herein, the term "heterocycle" refers to a monovalent chain of carbon and heteroatoms, wherein the heteroatoms are selected from nitrogen, oxygen, and sulfur, a portion of which, including at least one heteroatom, form a ring, such as tetrahydrofuran, aziridine, pyrrolidine, oxazolidine, 3-methoxypyrrolidine, 3-methylpiperazine, and the like.

As used herein, the term "acyl" refers to hydrogen, alkyl, cycloalkyl, alkenyl, cycloalkenyl, heterocyclyl, optionally substituted aryl, optionally substituted arylalkyl, optionally substituted heteroaryl, and optionally substituted heteroarylalkyl attached as a substituent through a carbonyl (C=O) group, such as formyl, acetyl, pivalolyl, benzoyl, phenacetyl, and the like.

As used herein, the terms "protected hydroxy" and "protected amino" refer to hydroxy and amino groups, respectively, that are protected with a protecting group. It is to be understood that such protecting groups are conventional and routinely selected to allow a synthetic or chemical transformation to be performed in a manner that the hydroxy group or amino group does not interfere with or is not changed by the synthetic or chemical transformation performed. Illustrative, but not exclusive, examples of such protecting groups may be found in Greene & Wuts "Protective Groups in Organic Synthesis," 2d Ed., John Wiley & Sons, New York, 1991, the disclosure of which is incorporated herein by reference. Further illustrative of such protecting groups are those particularly suited for protecting phenols and catechols, and analogs and derivatives thereof.

In another illustrative embodiment, compounds of formula I are described wherein when $R^a$ is 7-hydroxy, $R^c$ is not 4-hydroxy-3-(3-methylbut-2-enyl).

In another illustrative embodiment, compounds of formula I are described wherein when $R^a$ comprises 7-hydroxy, $R^c$ does not comprise 4'-hydroxy.

In another illustrative embodiment, compounds of formula I are described wherein $R^a$ includes at least one substituent selected from the group consisting of 7-hydroxy, 7-methoxy, 7-alkoxy and 7-substituted alkoxy; and $R^c$ is one or more alkoxy groups.

In another illustrative embodiment of the compounds of formula I, $R^a$ represents one or more substituents selected from optionally substituted alkoxy. In one aspect, $R^a$ represents at least two adjacent substituents taken together to form alkylenedioxy. In another embodiment, $R^a$ represents one or more substituents selected from halo, hydroxy, alkyl, nitro, and cyano.

In another illustrative embodiment of the compounds of formula I, $R^c$ represents one or more substituents selected from optionally substituted alkoxy. In one aspect, $R^c$ represents at least two adjacent substituents taken together to form alkylenedioxy. In another embodiment, $R^c$ represents one or more substituents selected from halo, hydroxy, and alkenyl, nitro, and cyano.

In another illustrative embodiment, compounds of formula I are described wherein $R^a$ represents one or more substituents selected from optionally substituted alkoxy and $R^c$ represents 4-methoxy-3-(3-methylbut-2-enyl) or 4-methoxy.

In another illustrative embodiment, a retrosynthetic analysis for compounds of formula I, exemplified by abyssinone II where $R^a$ is 7-hydroxy and $R^c$ is 4-hydroxy-3-(3-methylbut-2-enyl), is outlined in Scheme 1, wherein synthon compounds of formulae A and B contain $P_1$-protected and $P_2$-protected phenolic hydroxy groups, respectively. Such synthon compounds, illustratively based on 2,4-dihydroxyacetophenone and 3-bromo-4-hydroxybenzaldehyde, respectively, may be used to prepare compounds of formula I according to the processes described herein comprising aryl-allyl coupling, Claisen-Schmidt condensation, and isomeric cyclization.

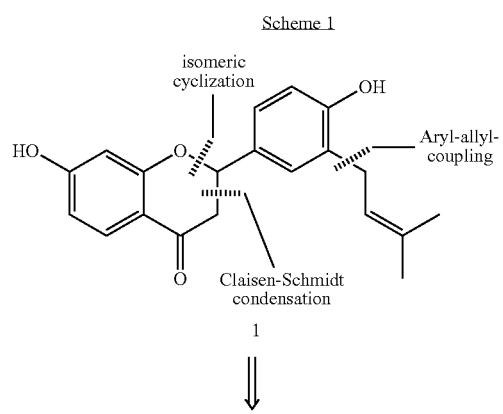

Scheme 1

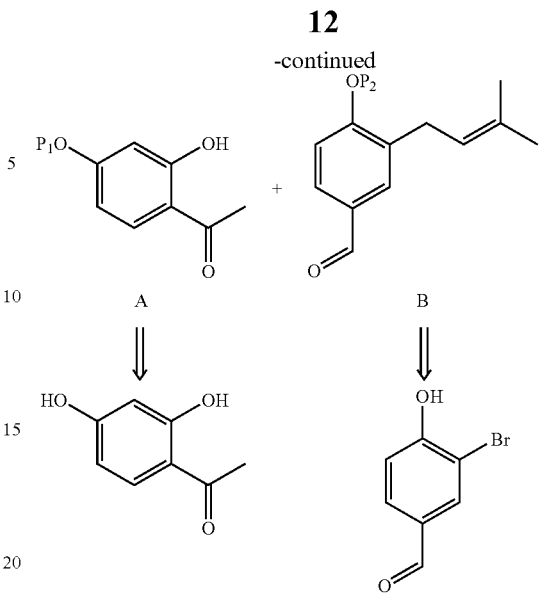

In another illustrative embodiment, 1,3-dioxolane-protected compounds 3a, 4a, 4b, 4c, and 4d are described. These compounds are prepared from 3-bromo-4-hydroxybenzaldehyde by the sequential protection process shown in Scheme 2, wherein aldehyde protection with ethylene glycol under acidic conditions using a Dean Stark trap affords bromophenol 3a. See, Mitsuru, S.; and Toshifumi. W. Preparation of Antihypertensive and Antianginal Phenyl Pyridyl Ketone Oximes and oxime ethers with potassium channel-opening activity. Eur. Pat. Appl. 1994, 130 pp. EP 623597 A1, the disclosure of which is incorporated herein by reference. Subsequent protection of the phenolic oxygen in bromophenol 3a with methoxymethylene chloride (MOMCl), dimethylsulfate, DHP, or TBDMS-Cl affords diprotected compounds 4a, 4b, 4c, and 4d, respectively.

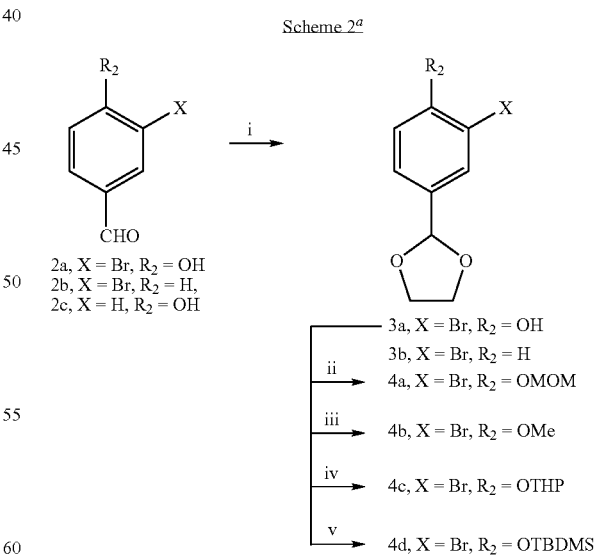

In another illustrative embodiment, exemplified for synthon B from Scheme 1, prenylated compounds 5a, 5b, 5c, 5d, 5e, and 5f are described. Several different approaches to aromatic prenylation, including Pd-catalyzed Stille coupling, pi-allyl nickel bromide complex mediated allylation, and allylation through aryl cuprate are described as shown in Scheme 3. See, Bach, T. and Kruger, L. The preparation of 2,3,5-tri and 2.3-disubstituted furans by regioselective plladium (0) catalyzed coupling reactions: Application to the syntheses of rosefuran and the F5 furan fatty acid. *Eur. J. Org. Chem.* 1999, 2045-2057; Kno"lker, H.-J.; Baum, E.; Reddy, K. R. *Tetrahedron Lett.* 2000, 41, 1171-1174; Tucker, C. E.; Majid, T. N.; Knochel, P. *J. Am. Chem. Soc.* 1992, 114, 3938-3984; Odejinmi, S. I. and Wiemer, D. F. Application of benzyl protecting groups in the synthesis of prenylated aromatic compounds. *Tetrahedron Lett.* 2005, 46, 3871-3874; Kyogoku, K. K.; Hatayama, K.; Yokomori, S.; Sek, T. and Tanaka, I. Synthesis of prenyl chalcone sophoradin, Isolated from *sophora subprostrata*. *Agric. Biol. Chem.* 1975, 1, 133-138; Jain, A. C. and Prasad, A. K. Synthesis of amorilin (euchrenone a3) and 5,7-dihydroxy-6",6"-dimethyl-6,8-di-C-prenylpyrano[2",3",4',3']flavanone. *Indan. J. Chem.* 1990, 29B, 525-528; Glusenkamp, K-H. and Buchi, G. C-prenylation of phenols promoted by aluminium oxide surfaces. *J. Org. Chem.* 1986, 51. 4481-4483, the disclosures of which are incorporated herein by reference. The prenylation step was found to be sensitive to modification of the reaction parameters as well as the steric environment created by the phenolic O-protecting group. As indicated in Table 1, the highest yield of prenylated product is observed with the use of CuBrDMS reagent at 0° C. to room temperature. After bromine-lithium exchange using n-BuLi, and subsequent transmetallation with CuBrDMS, the resulting cuprate is treated with phenylbromide to afford prenylated product. Whereas THP-protected compound 4c and TBDMS-protected compound 4d failed to produce any prenylated product, methoxymethyl (MOM) ether and methyl ether compounds 4a and 4b, respectively, provided the corresponding prenylation products in high yield.

Scheme 3

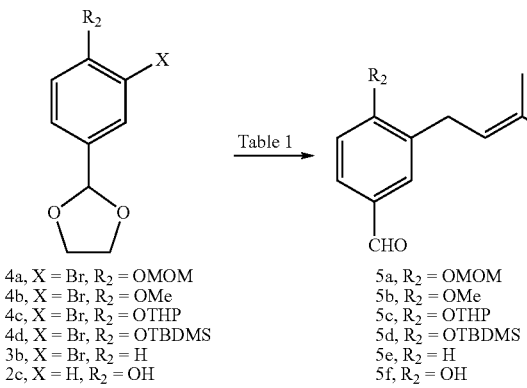

4a, X = Br, $R_2$ = OMOM
4b, X = Br, $R_2$ = OMe
4c, X = Br, $R_2$ = OTHP
4d, X = Br, $R_2$ = OTBDMS
3b, X = Br, $R_2$ = H
2c, X = H, $R_2$ = OH

5a, $R_2$ = OMOM
5b, $R_2$ = OMe
5c, $R_2$ = OTHP
5d, $R_2$ = OTBDMS
5e, $R_2$ = H
5f, $R_2$ = OH

TABLE 1

Aromatic prenylation yield using various starting materials and reaction conditions

| Starting Material | Reaction Conditions | Product | Yield |
|---|---|---|---|
| 2c | KOH/MeOH, 3,3-dimethyl allyl bromide, rt | 5f | 7% |
| 2c | $BF_3 \cdot OEt_2$, 3,3-dimethyl allyl bromide, rt | 5f | 4% |
| 2c | $BaO \cdot Al_2O_3$, 3,3-dimethyl allyl bromide, rt | 5f | 9% |

TABLE 1-continued

Aromatic prenylation yield using various starting materials and reaction conditions

| Starting Material | Reaction Conditions | Product | Yield |
|---|---|---|---|
| 4b | $Pd(PPh_3)_4$, tributyl(3-methyl-2butenyl)tin, 100° C. | 5b | 34%[a] |
| 4b | $Ni(COD)_2$, 3,3-dimethyl allyl bromide, rt | 5b | 8% |
| 4b | $^tBuLi$, CuCN•2LiCl, 3,3-dimethyl allyl bromide, rt | 5b | 45% |
| 4b | BuLi, CuBr•DMS, 3,3-dimethyl allyl bromide, 0° C.-rt | 5b | 85% |
| 4a | BuLi, CuBr•DMS, 3,3-dimethyl allyl bromide, rt | 5a | 83% |
| 4c | BuLi, CuBr•DMS, 3,3-dimethyl allyl bromide, rt | 5c | 0% |
| 4d | BuLi, CuBr•DMS, 3,3-dimethyl allyl bromide, rt | 5d | 0% |
| 3b | BuLi, CuBr•DMS, 3,3-dimethyl allyl bromide, −78° C. | 5e | 10%[b] |

[a] purification complicated by the presence of tributyl tin.
[b] Not optimized.

In another illustrative embodiment, exemplified for synthon A from Scheme 1, compounds 6a and 6b are described. These compounds are prepared by the process shown in Scheme 4, wherein 2,4-dihydroxyacetophenone is selectively monoprotected with methoxymethylene chloride (MOMCl) or dimethylsulfate, respectively, using $K_2CO_3$ in dry acetone.

Scheme 4

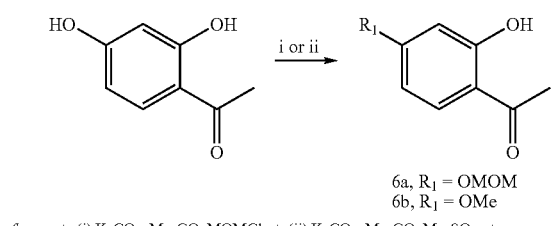

6a, $R_1$ = OMOM
6b, $R_1$ = OMe

[a] reagents (i) $K_2CO_3$, $Me_2CO$, MOMCl, rt. (ii) $K_2CO_3$, $Me_2CO$, $Me_2SO_4$, rt.

In another illustrative embodiment, compounds of formula I, i.e., flavanones 8a-8k, are prepared as outlined in Scheme 5A and Scheme 5B. Condensation of optionally substituted benzaldehyde 5 with optionally substituted acetophenone 6 under Claisen-Schmidt conditions using 60% KOH in methanol gave enone (i.e., chalcone) 7. Subsequent isomeric cyclization with NaOAc in refluxing ethanol provides the corresponding racemic flavanones 8, including racemic abyssinone II (8b).

It is appreciated that compounds 8a-8k and other compounds of formula I may be useful in treating various types of human cancers. It is also appreciated that compounds 8a, and 8c-8j may exhibit biological and pharmacological activity similar to that of racemic abyssinone II (8b). It is further appreciated that compounds 8a, and 8c-8j may be chemically more stable than racemic abyssinone II (8b), owing, at least in part, to the partial or complete absence of a phenolic hydroxy group.

Scheme 5A[a]

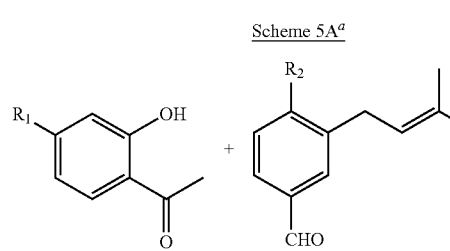

6a, R₁ = OMOM  
6b, R₁ = OMe  
6c, R₁ = H

5a, R₂ = OMOM  
5b, R₂ = OMe  
5c, R₂ = H

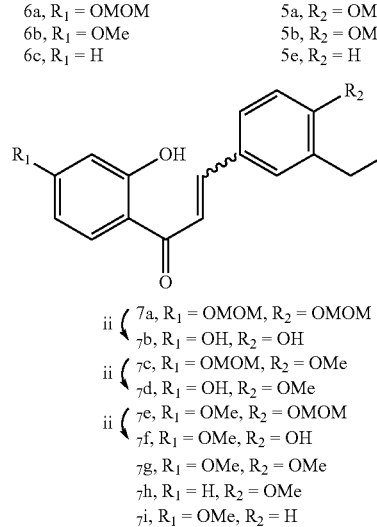

ii { 7a, R₁ = OMOM, R₂ = OMOM  
     7b, R₁ = OH, R₂ = OH  
ii { 7c, R₁ = OMOM, R₂ = OMe  
     7d, R₁ = OH, R₂ = OMe  
ii { 7e, R₁ = OMe, R₂ = OMOM  
     7f, R₁ = OMe, R₂ = OH  
7g, R₁ = OMe, R₂ = OMe  
7h, R₁ = H, R₂ = OMe  
7i, R₁ = OMe, R₂ = H

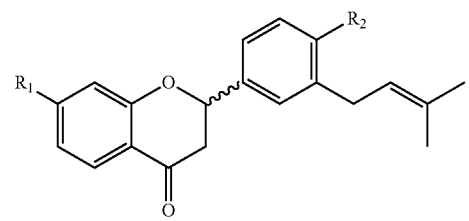

8a, R₁ = OMOM, R₂ = OMOM  
8b, R₁ = OH, R₂ = OH  
8c, R₁ = OMOM, R₂ = OMe  
8d, R₁ = OH, R₂ = OMe  
8e, R₁ = OMe, R₂ = OMOM  
8f, R₁ = OMe, R₂ = OH  
8g, R₁ = OMe, R₂ = OMe  
8h, R₁ = H, R₂ = OMe  
8i, R₁ = OMe, R₂ = H

Scheme 5B[a]

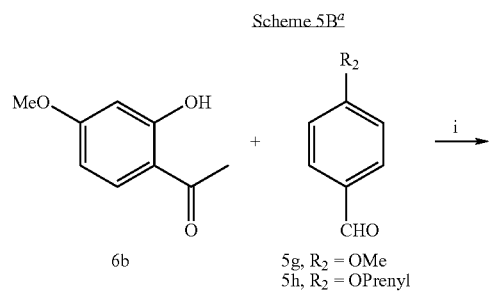

6b

5g, R₂ = OMe  
5h, R₂ = OPrenyl

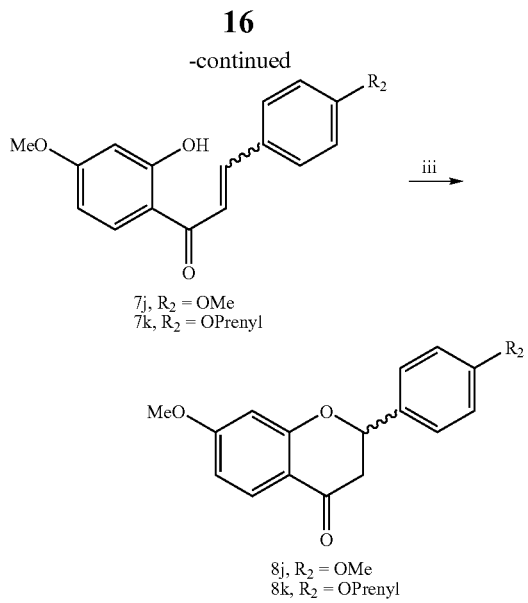

7j, R₂ = OMe  
7k, R₂ = OPrenyl

8j, R₂ = OMe  
8k, R₂ = OPrenyl

[a]reagents and conditions: (i) 60% aq. KOH (w/v)/MeOH, r. t. 24-36 h (ii) c. HCl, MeOH, r. t. 18-24 h (iii) NaOAC, EtOH, reflux, 24-48 h

Scheme 6[a]

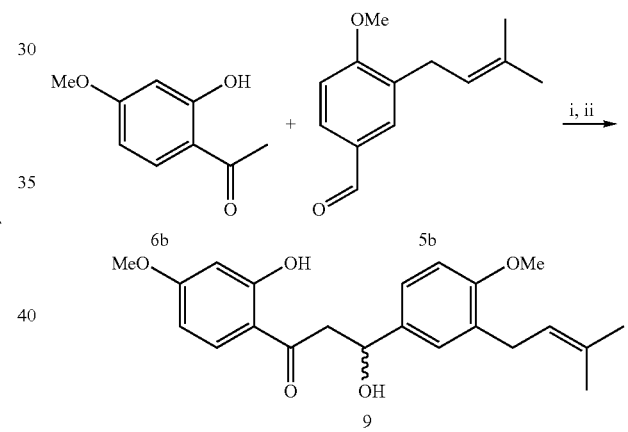

[a]reagents and conditions: (i) LiHMDS, THF, -20° C. to room temperature; (ii) aq NH₄Cl In another illustrative embodiment, compounds of formula II are described

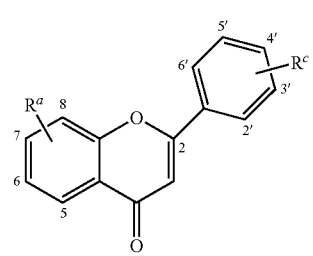

(II)

and pharmaceutically acceptable salts, hydrates, and solvates thereof, wherein:

$R^a$ represents 1-4 substituents each of which is independently selected from the group consisting of hydrogen, halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof; or $R^a$ represents 2-4 substituents where 2 of said substituents are adjacent substituents and are taken together with the attached carbons to form an optionally substituted heterocycle, and where the remaining substituents, in cases where $R^a$ represents 3-4 substituents, are each independently selected from the group consisting of hydrogen, halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof; and $R^c$ represents 1-4 substituents each of which is independently selected from the group consisting of hydrogen, halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof; or $R^c$ represents 2-4 substituents where 2 of said substituents are adjacent substituents and are taken together with the attached carbons to form an optionally substituted heterocycle, and where the remaining substituents, in cases where $R^c$ represents 3-4 substituents, are each independently selected from the group consisting of hydrogen, halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof.

In another illustrative embodiment, compounds of formula II are described wherein when $R^a$ is 5,6-dimethoxy, $R^c$ is not 2',6'-dimethoxy.

IN ANOTHER ILLUSTRATIVE EMBODIMENT, COMPOUNDS OF FORMULA II ARE DESCRIBED WHEREIN WHEN $R^A$ COMPRISES 5,6-DIMETHOXY, $R^C$ DOES NOT COMPRISE 2'-METHOXY. In another illustrative embodiment of the compounds of formula II, $R^a$ represents one or more substituents selected from optionally substituted alkoxy. In one aspect, $R^a$ represents at least two adjacent substituents taken together to form alkylenedioxy. In another embodiment, $R^a$ represents one or more substituents selected from halo, hydroxy, alkyl, nitro, and cyano.

In another illustrative embodiment of the compounds of formula II, $R^c$ represents one or more substituents selected from optionally substituted alkoxy. In one aspect, $R^c$ represents at least two adjacent substituents taken together to form alkylenedioxy. In another embodiment, $R^c$ represents one or more substituents selected from halo, hydroxy, alkyl, nitro, and cyano.

In another illustrative embodiment, a flavonoid compound of formula II, exemplified by zapotin where $R^a$ is 5,6-dimethoxy and $R^c$ is 2',6'-dimethoxy, is prepared as outlined in Scheme 7. 2-Hydroxy-6-methoxyacetophone is subjected to Elbs oxidation using sodium persulfate and aqueous sodium hydroxide to yield the substituted acetophenone 10. See, Wollenweber, E.; Iinuma, M.; Tanaka, T.; Mizuno, M. 5-Hydroxy-6,2'-dimethoxyflavone from Primula denticulata. Phytochemistry 1990, 29, 633-637, the disclosure of which is incorporated herein by reference. Subsequent regioselective methylation using anhydrous potassium carbonate and dimethyl sulfate in acetone affords 6-hydroxy-2,3-dimethoxyacetophenone 11. The yields of both steps improve when the mixtures are stirred for a prolonged period at room temperature; however, over-oxidation of the intermediate hydroquinone 10 is observed if the oxidation is carried out for more than one week. The generation of the dilithium dianion 12 of the acetophenone 11 is carried out with four equivalents of lithium hexamethyldisilylazide in THF. Treatment of dilithium dianion 12 with 2,6-dimethoxybenzoyl chloride 13, followed by acidification, affords the β-diketone intermediate 14, which is used without purification for cyclization to zapotin 15. The unpurified intermediate 14 is heated at 100° C. in the presence of glacial acetic acid containing 0.5% sulfuric acid for 3.5 h to provide zapotin 15 on multi-gram scale in high yield.

It is appreciated that zapotin 15 and other compounds of formula II may be useful in treating various types of human cancers. It is also appreciated that analogues of zapotin may exhibit biological and pharmacological activity similar to that of zapotin 15. It is further appreciated that Scheme 7 is amenable to a wide variety of $R^a$ and $R^c$ substituents.

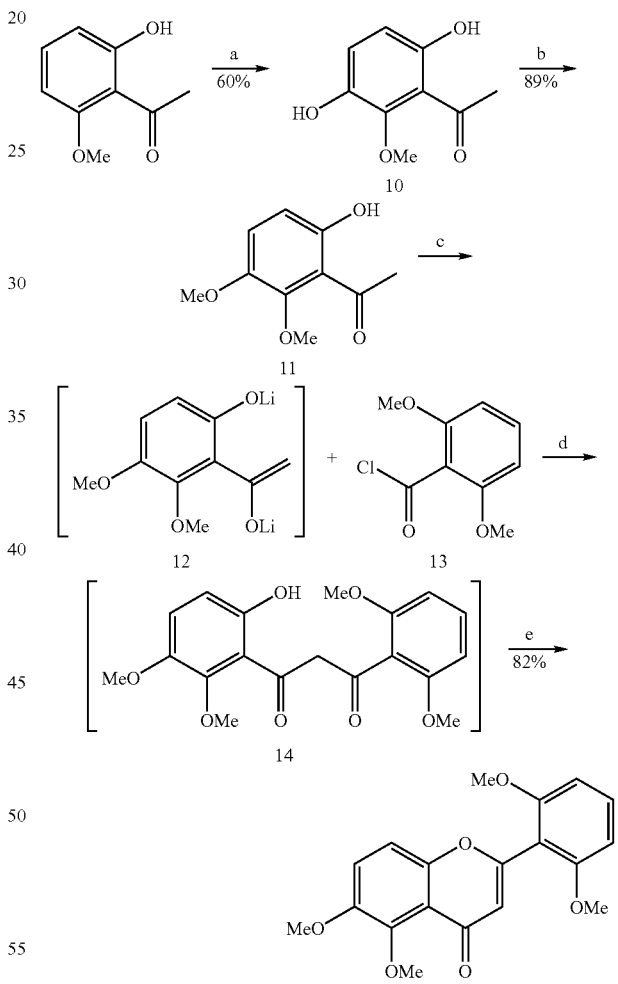

[a]Reagents and conditions: (a) (1) NaOH, K$_2$S$_2$O$_8$, 20° C. (7d), (2) aq HCl; (b) K$_2$CO$_3$, Me$_2$SO$_4$, Me$_2$CO (7d); (c) Compound 9, LiHMDS, THF, -78° C. to -10° C., (3 h), (1.5 h); (d) Compound 11, -78° C. to 23° C. (25 h), (2) aq HCl; (e) H$_2$SO$_4$, AcOH, 95° C. to 100° C. (3.5 h).

The flavonoid compounds described herein may also form hydrates and solvates. Hydrates may be formed spontaneously upon exposure to ambient conditions where the humidity is sufficient to hydrate the compounds. In addition, hydrates may be formed with more specificity by exposing the compounds described herein to particular humidity conditions. Hydrates may also be formed with by dissolving or suspending the compounds in media containing a predetermined amount of water and evaporating, lyophilizing, or otherwise concentrating such solutions in a manner to give a hydrate form of the compounds described herein. Solvates of the flavonoid compounds described herein may also be formed by dissolving or suspending the compounds in a solvent that is capable of forming a complex with the compound, and subsequently evaporating or otherwise concentrating such solutions in a manner to give a solvate form of the compounds described herein. Solvents capable of forming solvates may include alcohols, such as ethanol, butanol, and the like. It is appreciated that both hydrates and solvates of the flavonoid compounds described herein may have a predetermined stoichiometry. Such stoichiometry may be evaluated by conventional analytical techniques, including X-ray diffraction, melting analysis, and the like.

Also described herein are pharmaceutical compositions and formulations comprising a therapeutically effective amount of one or more flavonoid compounds described herein for treating a patient having cancer. It is appreciated that mixtures of certain flavonoid compounds described herein may be administered. Such pharmaceutical compositions may also include one or more diluents, carriers, and/or excipients. As used herein, an effective amount of the flavonoid compound is defined as the amount of the compound which, upon administration to a patient, inhibits growth of cancer cells, kills malignant cells, reduces the volume or size of the tumors, and/or eliminates the tumor entirely in the treated patient. It is to be understood that treated patients include humans and other mammals.

As used herein, the term "therapeutically effective amount" refers to the amount to be administered to a patient, and may be based on body surface area, patient weight, and/or patient condition. In addition, it is appreciated that there is an interrelationship of dosages determined for humans and those dosages determined for animals, including test animals (illustratively based on milligrams per meter squared of body surface) as described by Freireich, E. J., et al., *Cancer Chemother. Rep.* 1966, 50 (4), 219, the disclosure of which is incorporated herein by reference. Body surface area may be approximately determined from patient height and weight (see, e.g., Scientific Tables, Geigy Pharmaceuticals, Ardley, N.Y., pages 537-538 (1970)). A therapeutically effective amount of the flavonoid compounds described herein may be defined as any amount useful for inhibiting the growth of (or killing) a population of malignant cells or cancer cells, such as may be found in a patient in need of relief from such cancer or malignancy. Typically, such effective amounts range from about 5 mg/kg to about 500 mg/kg, from about 5 mg/kg to about 250 mg/kg, and/or from about 5 mg/kg to about 150 mg/kg of flavonoid compounds per patient body weight. It is appreciated that effective doses may also vary depending on the route of administration, optional excipient usage, and the possibility of co-usage of the flavonoid compounds with other conventional and non-conventional therapeutic treatments, including other anti-tumor agents, radiation therapy, and the like.

The flavonoid compounds described herein may be administered in a variety of pharmaceutical formulations, including conventional pharmaceutical formulations. The flavonoid compounds, and formulated variants thereof, may also be delivered by a variety of administration routes, including conventional delivery routes. In one embodiment, the flavonoid compounds, and formulated variants thereof, are delivered via a parenteral route, including subcutaneously, intraperitoneally, intramuscularly, and intravenously. Examples of parenteral dosage forms and formulations include aqueous solutions of the flavonoid compounds in isotonic saline, 5% glucose or other conventional pharmaceutically acceptable liquid carrier. In one aspect, one or more flavonoid compounds are dissolved in a saline solution containing 5% dimethyl sulfoxide and 10% Cremphor EL (Sigma Chemical Company). Additional solubilizing agents such as cyclodextrins, which can form specific, more soluble complexes with the flavonoid compounds described herein, or other conventional solubilizing agents can be included as pharmaceutical excipients for delivery of the compounds.

In another embodiment, the flavonoid compounds described herein, and formulated variants thereof, are delivered via oral administration, such as in a capsule, a gel seal, a tablet, and the like. Capsules may comprise any conventional pharmaceutically acceptable material including gelatin and/or cellulose derivatives. Tablets may be formulated by conventional procedures, including by compressing mixtures of the flavonoid compounds, solid carriers, lubricants, disintegrants, and other conventional ingredients for solid dosage forms, such as starches, sugars, bentonite, and the like. The flavonoid compounds described herein may also be administered in a form of a hard shell tablet or capsule containing, for example, lactose or mannitol as a binder, and conventional fillers and tableting agents. Solid dosage forms described herein and useful for delivering the flavonoid compounds described herein also include sustained release formulations, such as tablets, caplets, pills, capsules, and the like that include an enteric coating that may delay the release of the flavonoid compounds until the formulation has passed into the intestinal tract.

The following exemplary embodiments are included herein to further illustrate the invention. These exemplary embodiments are not intended and should not be interpreted to limit the scope of the invention in any way. It is to be understood that numerous variations of these exemplary embodiments are contemplated herein.

COMPOUND EXAMPLES

NMR spectra were obtained at 300 MHz ($^1$H) and 75 MHz ($^{13}$C) in CDCl$_3$ using CHCl$_3$ as internal standard. Flash chromatography was performed with 230-400 mesh silica gel. TLC was carried out using commercially available precoated glass silica gel plates of 2.5 mm thickness. Melting points are uncorrected. Unless otherwise stated, chemicals and solvents were of reagent grade and used as obtained from commercial sources without further purification. Tetrahydrofuran (THF) and diethyl ether were freshly distilled from sodium/benzophenone ketyl radical prior to use. Acetone was freshly distilled from potassium carbonate prior to use. Benzene was distilled from phosphorous pentoxide prior to use.

2-Bromo-4-(1,3-dioxolan-2-yl)phenol (3a). 3-Bromo-4-hydroxybenzaldehyde (2a, 10.0 g, 49.8 mmol) was heated at reflux with 1,2-dihydroxyethane (25 g, 0.4 mol) in toluene (150 mL) in the presence of p-toluenesulfonic acid (950 mg) for 48 h in an apparatus fitted with a Dean-Stark trap. The reaction mixture was concentrated by reduced pressure evaporation, washed with aqueous sodium hydrogen carbonate, water, brine, dried over Na$_2$SO$_4$, evaporated to dryness and then passed through a short silica gel column using a hexanes-ethyl acetate mixture (5:1) with a few drops of triethylamine as eluent to afford the protected product 3a (11.0 g, 95%) as a crystalline solid. R$_f$=0.38 (25% EtOAc-hexanes): mp 76-78° C. IR (neat) 3351, 2954, 2891, 1608, 1499, 1431, 1284, 1100 cm$^{-1}$; $^1$H NMR (300 MHz, CDCl$_3$) δ 7.57

(d, J=1.8 Hz, 1H), 7.28 (dd, J=8.4, 2.4 Hz, 1H), 6.96 (d, J=8.7 Hz, 1H), 5.69 (s, 1H), 4.03 (m, 4H); $^{13}$C NMR (75 MHz, CDCl$_3$) δ 152.9, 131.5, 130.2, 127.5, 115.8, 110.0, 102.7, 65.2; CIMS (m/z, rel intensity) 247 (MH$^+$+2, 7), 245 (MH$^+$, 7), 203 (100), 201 (100), 175 (4), 173(5), 94 (1).

2-(3-Bromo-4-(methoxymethoxy)phenyl)-1,3-dioxolane (4a). ($^i$Pr)$_2$NEt (6.0 mL, 35.0 mmol) was added dropwise to a stirred and cooled (0° C.) solution of alcohol 3a (4.0 g, 16.3 mmol) in CH$_2$Cl$_2$ (50 mL). After 15 min methoxymethylene chloride (MOMCl) (1.6 mL, 28 mmol) was added dropwise over a period of 5 min, and stirring was continued for 1 h. The cold bath was removed, and stirring was continued for 12 h. The reaction mixture was diluted with water (10 mL) and extracted with CH$_2$Cl$_2$. The combined organic extracts were washed with brine, dried over Na$_2$SO$_4$, and evaporated. The residue was purified by flash chromatography using hexanes-ethyl acetate mixture (5:1) as eluent to give compound 4a (4.4 g, 94%) as a colorless liquid. R$_f$=0.48 (25% EtOAc-hexanes); IR (neat) 2956, 2889, 1606, 1497, 1246, 1100, 1043 cm$^{-1}$; $^1$H NMR (300 MHz, CDCl$_3$) δ 7.64 (d, J=1.8 Hz, 1H), 7.31 (dd, J=8.7, 2.1 Hz, 1H), 7.10 (d, J=8.1 Hz, 1H), 5.70 (s, 1H), 5.21 (s, 2H), 4.02 (m, 4H), 3.46 (s, 3H); $^{13}$C NMR (75 MHz, CDCl$_3$) δ 154.2, 132.8, 131.4, 126.7, 115.5, 112.6, 102.5, 94.8, 65.1, 56.2; EIMS (m/z, rel intensity) 290 (M$^+$+2, 54), 288 (M$^+$, 58), 259 (23), 257 (23), 209 (56), 73 (100).

2-(3-Bromo-4-methoxyphenyl)-1,3-dioxolane (4b). A mixture of 2-bromo-4-(1,3-dioxolan-2-yl)phenol (3a, 2.0 g, 8.2 mmol) and oven-dried potassium carbonate (2.7 g, 20.0) in dry acetone (20 mL) was stirred for 10 min. Dimethyl sulfate (0.9 mL, 10.0 mmol) was added dropwise to the reaction mixture and the mixture was stirred at room temperature for 18 h. Excess potassium carbonate was filtered off and washed with acetone (3×10 mL). Solvent was evaporated under reduced pressure and water (25 mL) was added. The mixture was extracted with chloroform (3×100 mL) and the organic phase was dried over Na2SO4 and evaporated under reduced pressure. The residue was column chromatographed on silica gel eluting with 20% ethyl acetate in hexanes to afford compound 4b (1.9 g, 91% yield) as a colorless oil. R$_f$=0.51 (25% EtOAc-hexanes); $^1$H NMR (300 MHz, CDCl$_3$) δ 7.63 (d, J=2.1 Hz, 1H), 7.33 (dd, J=8.4, 2.1 Hz, 1H), 6.83 (d, J=8.1 Hz, 1H), 5.68 (s, 1H), 4.02 (m, 4H), 3.84 (s, 3H); $^{13}$C NMR (75 MHz, CDCl$_3$) δ 156.3, 131.3, 126.8, 111.3, 102.6, 65.1, 56.1.

General procedure A for prenylation to make compounds (5a-5d). Diprotected bromo compound (6.9 mmol) was dissolved in benzene (18 mL), and anhydrous ether (36 mL) and molecular sieves (1.0 g) were added. After dropwise addition of n-BuLi (3.2 mL, 2.5 M in hexanes, 8.0 mmol) at 0° C., the reaction mixture was stirred for another 30 min at room temperature and then solid CuBr•DMS (700 mg, 3.5 mmol) was added carefully while cooling the reaction mixture on an ice water bath. The reaction mixture was allowed to stir for 60 min at room temperature and then prenyl bromide (1.0 mL, 8.3 mmol) was added. After the reaction mixture was stirred for 5 h, it was quenched by addition of saturated NH$_4$Cl (10 mL), followed by addition of 1 N HCl (10 mL), and the mixture was stirred for 20 min. The aqueous layer was extracted with ether and washed with 20% aqueous acetic acid (20 mL) and then concentrated in vacuo. Most of the ketal converted to aldehyde during this process. The initial oil was taken in CH$_2$Cl$_2$ (15 mL) and SiO$_2$ (1.0 g, mmol) and the mixture was stirred for 30 min at room temperature for complete ketal deprotection. The solvent was removed and the solid was directly poured at the top of a silica gel column for purification eluting with 25% ethyl acetate in hexanes to afford prenylated aldehyde as light yellow oil.

4-(Methoxymethoxy)-3-(3-methylbut-2-enyl)benzaldehyde (5a). The compound was isolated as clear light yellow oil in 83% yield. R$_f$=0.58 (25% EtOAc-hexanes); IR (neat) 2912, 1689, 1599, 1494, 1255, 1151 cm$^{-1}$; $^1$H NMR (300 MHz, CDCl$_3$) δ 9.83 (s, 1H), 7.64 (m, 2H), 7.14 (d, J=9.3 Hz, 1H), 5.26 (s, 2H), 5.25 (m, 1H), 3.45 (s, 3H), 3.34 (d, J=7.2 Hz, 2H), 1.72 (s, 3H), 1.69 (s, 3H); $^{13}$C NMR (75 MHz, CDCl$_3$) δ 191.2, 159.8, 133.4, 131.5, 130.6, 130.3, 130.2, 121.3, 113.1, 93.9, 56.2, 28.5, 25.8, 17.7; EIMS (m/z, rel intensity) 234 (M$^+$, 17), 202 (100), 187 (62), 173 (36), 159 (56), 91(27).

4-Methoxy-3-(3-methylbut-2-enyl)benzaldehyde (5b). The compound was isolated as clear light yellow oil in 85% yield. R$_f$=0.62 (25% EtOAc-hexanes); IR (neat) 2966, 2914, 2733, 1687, 1599, 1579, 1497, 1441, 1255, 1160 cm$^{-1}$; $^1$H NMR (CDCl$_3$) δ 9.79 (s, 1H), 7.63 (m, 2H), 6.87 (d, J=8.4 Hz, 1H), 5.24 (t, J=7.2 Hz, 2H), 3.85 (s, 3H), 3.28 (d, J=1.2 Hz, 2H), 1.70 (s, 3H), 1.65 (s, 3H); $^{13}$C NMR (75 MHz, CDCl$_3$) δ 190.9, 162.2, 133.3, 130.8, 130.5, 130.0, 129.4, 121.1, 114.1, 55.5, 28.0, 25.6, 17.6.

1-(2-Hydroxy-4-(methoxymethoxy)phenyl)ethanone (6a). A mixture of 2,4-dihydroxy acetophenone (2.0 g, 13.2 mmol) and oven-dried potassium carbonate (4.0 g, 30.0 mmol) in dry acetone (30 mL) was stirred for 10 min. Methoxymethylene chloride (MOMCl) (1.62 mL, 17.2 mmol) was added dropwise to the reaction mixture and the mixture was stirred at room temperature for 24 h. Solvent was evaporated under reduced pressure and water (25 mL) was added. The mixture was extracted with chloroform (3×100 mL) and the organic phase was dried over Na$_2$SO$_4$ and evaporated under reduced pressure. The residue was column chromatographed on silica gel eluting with 20% ethyl acetate in hexanes to afford acetophenone 6a (2.2 g, 87% yield) as a very low melting solid. R$_f$=0.51 (25% EtOAc-hexanes): mp 38-39° C. IR (KBr) 2959, 2829, 1632, 1579, 1504, 1367, 1262, 1142 cm$^{-1}$; $^1$H NMR (300 MHz, CDCl$_3$) δ 7.59 (d, J=8.7 Hz, 1H), 6.51 (m, 2H), 5.15 (s, 2H), 3.42 (s, 3H), 2.51 (s, 3H); $^{13}$C NMR (75 MHz, CDCl$_3$) δ 202.6, 164.7, 163.4, 132.3, 114.6, 108.0, 103.6, 93.8, 56.2, 26.1; EIMS (m/z, rel intensity) 196 (M$^+$, 100), 181 (6), 164 (9), 151 (32), 137 (24).

1-(2-Hydroxy-4-methoxyphenyl)ethanone (6b). A mixture of 2,4-dihydroxy-acetophenone (1.0 g, 6.6 mmol) and oven-dried potassium carbonate (1.0 g, 7.6 mmol) in dry acetone (20 mL) was stirred for 10 min. Dimethyl sulfate (0.62 mL, 6.6 mmol) was added dropwise to the reaction mixture and the mixture was stirred at room temperature for 12 h. Solvent was evaporated under reduced pressure and water (25 mL) was added. The mixture was extracted with chloroform (3×100 mL) and the organic phase was dried over Na$_2$SO$_4$ and evaporated under reduced pressure. The residue was column chromatographed on silica gel eluting with 20% ethyl acetate in hexanes to afford compound 6b (960 mg, 88% yield) as a crystalline solid. R$_f$=0.55 (20% EtOAc-hexane); mp 48° C. (lit 49-50° C.); $^1$H NMR (300 MHz, CDC$_{l3}$) δ 7.63 (d, J=9.0 Hz, 1H), 6.40 (m, 2H), 3.87 (s, 3H), 2.58 (s, 3H).

General procedure B for synthesis of chalcones 7a, 7c, 7e, 7g-7j. A solution of 60% aqueous KOH (1.5 mL) was added dropwise to a well-stirred mixture of acetophenone 6 (1.0 mmol) and aldehyde 5 (1.0 mmol) at room temperature. After 12-14 h, the pH of the reaction mixture was brought back to 7.0 by careful addition of 1 N HCl solution (~5 mL). The aqueous layer was extracted with ethyl acetate, washed with brine, dried (Na$_2$SO$_4$), and then concentrated in vacuo. The residue was column chromatographed eluting with 15% ethyl acetate in hexanes to afford chalcones 7 in high yield.

1-(2-Hydroxy-4-(methoxymethoxy)phenyl)-3-(4-(methoxymethoxy)-3-(3-methylbut-2-enyl)phenyl)prop-2-en-1- one (7a). The compound was isolated as yellow semisolid in 76% yield. $R_f$=0.26 (15% EtOAc-hexanes); IR (neat) 2910, 1634, 1571, 1497, 1359, 1242, 1151, 1077, 997 cm$^{-1}$; $^1$H NMR (300 MHz, CDCl$_3$) δ 7.84 (dd, J=12.3, 3.3 Hz, 2H), 7.44 (m, 3H), 7.07 (d, J=9.0 Hz, 1H), 6.60 (m, 2H), 5.28 (t, J=7.2 Hz, 1H), 5.22 (s, 2H), 5.19 (s, 2H), 3.45 (s, 6H), 3.34 (d, J=7.2 Hz, 2H), 1.73 (s, 3H), 1.72 (s, 3H); $^{13}$C NMR (75 MHz, CDCl$_3$) δ 192.0, 166.0, 163.3, 157.1, 144.7, 133.0, 131.3, 130.1, 128.0, 127.8, 121.8, 117.8, 114.9, 113.7, 108.0, 103.8, 93.9, 56.3, 56.1, 28.6, 25.7, 17.8; EIMS (m/z, rel intensity) 412 (M$^+$, 81), 380 (12), 367 (16), 219 (67), 187 (100), 181 (55), 151 (36), 69 (45); HRMS m/z calcd for $C_{24}H_{28}O_6$ 412.1886; found 412.2884. Anal. Calcd for $C_{24}H_{28}O_6$·1.75H2O: C, 64.92; H, 7.15. Found: C, 65.08; H, 6.79.

1-(2-Hydroxy-4-(methoxymethoxy)phenyl)-3-(4-methoxy-3-(3-methylbut-2-enyl)phenyl)prop-2-en-1-one (7c). The compound was isolated as yellow semi solid in 65% yield. $R_f$=0.52 (20% EtOAc-hexanes); IR (neat) 2912, 2837, 1682, 1634, 1568, 1502, 1361, 1255, 1233, 1155, 1079, 999 cm$^{-1}$; $^1$H NMR (300 MHz, CDCl$_3$) δ 7.84 (d, J=5.8 Hz, 1H), 7.80 (s, 1H), 7.46 (dd, J=9.0, 2.4 Hz, 1H), 7.42 (d, J=5.1 Hz, 1H), 7.38 (s, 1H), 6.85 (d, J=8.4 Hz, 1H), 6.60 (d, J=2.1 Hz, 1H), 6.56 (dd, J=8.7, 2.1 Hz, 1H), 5.27 (t, J=6.9 Hz, 1H), 5.19 (s, 2H), 3.85 (s, 3H), 3.46 (s, 3H), 3.31 (d, J=7.2 Hz, 2H), 1.74 (s, 3H), 1.70 (s, 3H); $^{13}$C NMR (75 MHz, CDCl$_3$) δ 191.9, 166.0, 163.2, 159.6, 144.9, 133.0, 131.1, 130.7, 129.6, 128.3, 126.9, 121.6, 117.1, 114.9, 110.2, 107.9, 103.8, 93.8, 56.2, 55.4, 28.3, 25.7, 17.7; CIMS (m/z, rel intensity) 383 (MH$^+$, 100), 351 (12), 327 (17), 229 (30), 181 (51), 151 (11); HRMS m/z calcd for $C_{23}H_{26}O_5$ 382.1780; found 382.1783. Anal. Calcd for $C_{23}H_{26}O_5$·1.0H$_2$O: C, 68.98; H, 7.05. Found: C, 69.08; H, 7.04.

1-(2-Hydroxy-4-methoxyphenyl)-3-(4-(methoxymethoxy)-3-(3-methylbut-2-enyl)phenyl)prop-2-en-1-one (7e). The compound was isolated as yellow semi solid in 80% yield. $R_f$=0.55 (25% EtOAc-hexanes); IR (neat) 2923, 2853, 1634, 1578, 1497, 1363, 1221, 1152, 1129, 1078 cm$^{-1}$; $^1$H NMR (300 MHz, CDCl$_3$) δ 7.83 (d, J=7.2 Hz, 2H), 7.42 (m, 3H), 7.06 (d, J=8.4 Hz, 1H), 6.47 (d, J=2.7 Hz, 1H), 6.44 (d, J=2.4 Hz, 1H), 5.29 (t, J=6.9 Hz, 1H), 5.23 (s, 2H), 3.82 (s, 3H), 3.45 (s, 3H), 3.33 (d, J=7.2 Hz, 2H), 1.73 (s, 3H), 1.71 (s, 3H); $^{13}$C NMR (75 MHz, CDCl$_3$) δ 191.9, 166.5, 165.9, 157.0, 144.6, 133.0, 131.3, 131.1, 130.1, 128.1, 127.8, 121.8, 117.9, 114.1, 113.7, 107.6, 101.0, 94.0, 56.1, 55.5, 28.7, 25.8, 17.8; EIMS (m/z, rel intensity) 382 (M$^+$, 44), 350 (7), 337 (11), 219 (30), 187 (52), 151 (100), 69 (83); HRMS m/z calcd for $C_{23}H_{26}O_5$ 382.1780; found 382.1779. Anal. Calcd for $C_{23}H_{26}O_5$·0.5H$_2$O: C, 70.57; H, 6.95. Found: C, 70.45; H, 7.27.

1-(2-Hydroxy-4-methoxyphenyl)-3-(4-methoxy-3-(3-methylbut-2-enyl)phenyl)prop-2-en-1-one (7g). The compound was isolated as yellow oil in 75% yield. $R_f$=0.48 (25% EtOAc-hexanes): mp 82-84° C. IR (neat) 2964, 2944, 1633, 1567, 1504, 1442, 1362, 1252, 1219, 1128, 1121 cm$^{-1}$; $^1$H NMR (300 MHz, CDCl$_3$) δ 7.83 (d, J=8.7 Hz, 1H), 7.79 (d, J=2.1 Hz, 1H), 7.47 (dd, J=8.1, 2.1 Hz, 1H), 7.42 (d, J=4.8 Hz, 1H), 7.39 (d, J=8.7 Hz, 1H), 6.85 (d, J=9.0 Hz, 1H), 6.48 (d, J=2.4 Hz, 1H), 6.44 (d, J=2.4 Hz, 1H), 5.27 (t, J=7.2 Hz, 1H), 3.85 (s, 3H), 3.83 (s, 3H), 3.31 (d, J=7.2 Hz, 2H), 1.74 (s, 3H), 1.70 (s, 3H); $^{13}$C NMR (75 MHz, CDCl$_3$) δ 191.9, 166.5, 165.9, 144.8, 133.1, 131.1, 130.8, 129.6, 128.3, 127.1, 121.7, 117.3, 114.1, 110.3, 107.5, 101.0, 55.5, 28.4, 25.8, 17.8; EIMS (m/z, rel intensity) 352 (M$^+$, 100), 321 (25), 283 (14), 202 (18), 189 (100), 115 (18), 69 (35); HRMS m/z calcd. for $C_{22}H_{24}O_4$ 352.1675; found 324.1675. Anal. Calcd for $C_{22}H_{24}O_4$·3.0H$_2$O: C, 65.01; H, 7.44. Found: C, 65.30; H, 7.41.

1-(2-Hydroxyphenyl)-3-(4-methoxy-3-(3-methylbut-2-enyl)phenyl)prop-2-en-1-one (7h). The compound was isolated as yellow semi solid in 55% yield. $R_f$=0.5 (15% EtOAc-hexanes): IR (neat) 3428, 2934, 1714, 1661, 1497, 1416, 1391, 1256, 1103 cm$^{-1}$; $^1$H NMR (300 MHz, CDCl$_3$) δ 7.90 (d, J=5.4 Hz, 1H), 7.84 (s, 1H), 7.50 (m, 3H), 7.43 (s, 1H), 6.99 (d, J=8.1 Hz, 1H), 6.91 (t, J=7.5 Hz, 1H), 6.85 (d, J=8.4 Hz, 1H), 5.28 (t, J=7.2 Hz, 1H), 3.86 (s, 3H), 3.31 (d, J=7.2 Hz, 2H), 1.74 (s, 3H), 1.70 (s, 3H); $^{13}$C NMR (75 MHz, CDCl$_3$) δ 193.7, 163.5, 159.9, 145.9, 136.0, 133.2, 130.9, 129.8, 129.5, 128.5, 126.9, 121.6, 120.1, 118.7, 117.1, 110.3, 55.5, 28.4, 25.8, 17.8; EIMS (m/z, rel intensity) 322 (M$^+$, 35), 291 (10), 253 (14), 189 (34), 171 (12), 147 (31), 121 (89), 115 (24), 69 (100); HRMS m/z calcd. for $C_{21}H_{22}O_3$ 322.1569; found 322.1575.

1-(2-Hydroxy-4-methoxyphenyl)-3-(3-(3-methylbut-2-enyl)phenyl)prop-2-en-1-one (7i). The compound was isolated as yellow semi solid in 81% yield. $R_f$=0.5 (15% EtOAc-hexanes): IR (neat) 3420, 2964, 1634, 1574, 1505, 1441, 1359, 1260, 1233, 1127 cm$^{-1}$; $^1$H NMR (300 MHz, CDCl3) δ 7.82 (m, 2H), 7.47 (m, 3H), 7.30 (t, J=7.5 Hz, 1H), 7.21 (d, J=8.7 Hz, 1H), 6.47 (d, J=2.1 Hz, 1H), 6.44 (s, 1H), 5.31 (t, J=6.0 Hz, 1H), 3.82 (s, 3H), 3.35 (d, J=7.2 Hz, 2H), 1.74 (s, 3H), 1.71 (s, 3H); $^{13}$C NMR (75 MHz, CDCl$_3$) δ 191.8, 166.6, 166.1, 144.7, 142.6, 134.7, 133.2, 131.2, 130.8, 128.9, 128.6, 125.8, 122.5, 120.0, 114.0, 107.7, 101.0, 55.5, 34.1, 25.7, 17.8; EIMS (m/z, rel intensity) 322 (M$^+$, 74), 305 (6), 253 (22), 177 (100), 151 (77), 115 (18), 95 (18), 69 (24); HRMS m/z calcd. for $C_{21}H_{22}O_3$ 322.1569; found 322.1567.

1-(2-Hydroxy-4-methoxyphenyl)-3-(4-methoxyphenyl)prop-2-en-1-one (7j). The compound was isolated as crystalline bright yellow solid in 85% yield. $R_f$=0.52 (15% EtOAc-hexanes): mp 106-108° C. IR (KBr) 3002, 2956, 2935, 2832, 1632, 1569, 1510, 1442, 1365, 1283, 1258, 1220, 1171, 1128 cm$^{-1}$; $^1$H NMR (300 MHz, CDCl$_3$) δ 7.81 (m, 2H), 7.58 (m, 2H), 7.43 (d, J=15.3 Hz), 1H), 6.91 (m, 2 H), 3.83 (s, 3H), 3.82 (s, 3H); $^{13}$C NMR (75 MHz, CDCl$_3$) δ 191.8, 166.5, 165.9, 161.7, 144.2, 131.0, 130.3, 127.4, 117.7, 114.4, 114.1, 107.5, 101.0, 55.5, 55.4; ESIMS (m/z, rel intensity) 285 (MH$^+$, 100), 267 (1), 239 (1), 160 (10), 151 (14), 150 (9); EIHRMS m/z calcd. for $C_{17}H_{16}O_4$ 284.1049; found 284.1047. Anal. Calcd for $C_{17}H_{16}O_4$: C, 71.85; H, 5.67. Found: C, 71.85; H, 5.70.

1-(2-Hydroxy-4-methoxyphenyl)-3-(4-(3-methylbut-2-enyloxy)phenyl)prop-2-en-1-one (7k). The compound was isolated as bright yellow crystalline solid in 80% yield: mp 95-97° C. Rf=0.5 (15% EtOAc-hexanes); IR (KBr) 3052, 2917, 2849, 1633, 1604, 1578, 1566, 1508, 1363, 1264, 1219, 1172, 1128, 1019 cm 1; $^1$H NMR (300 MHz, CDCl3) □ 7.82 (m, 2H), 7.57 (m, 2H), 7.44 (d, J=15.6 Hz, 1H), 6.93 (m, 2H), 6.44 (m, 2H), 5.46 (m, 1H), 4.53 (d, J=6.6 Hz, 2H), 3.82 (s, 3H), 1.78 (s, 3H), 1.73 (s, 3H); $^{13}$C NMR (75 MHz, CDCl3) □ 191.8, 166.5, 165.9, 161.1, 144.3, 138.8, 131.0, 130.3, 127.3, 119.0, 117.6, 115.0, 114.0, 107.5, 101.0, 64.9, 55.5, 25.8, 18.2; ESIMS (m/z, rel intensity) 339 (MH+, 100), 271 (30), 215 (7), 151 (1); EIHRMS m/z calcd. for C17H16O4 284.1049; found 284.1047.

General procedure C for deprotection of the MOM group from chalcones to synthesize 7b, 7d, 7f. Concd HCl (0.25 mL/MOM group) was added to a solution of chalcone (1 mmol) in methanol (10 mL) at room temperature and the reaction mixture was stirred for 24-36 h until disappearance of starting material. The solvent was evaporated under reduced pressure and the residue was column chromatographed eluting with 25% ethyl acetate in hexanes to afford flavanone in high yield.

1-(2,4-Dihydroxyphenyl)-3-(4-hydroxy-3-(3-methylbut-2-enyl)phenyl)-prop-2-en-1-one (7b). The compound was isolated as crystalline bright reddish yellow solid in 95% yield. $R_f$=0.47 (25% EtOAc-hexanes): mp 167° C. IR (KBr) 3302, 2966, 2925, 1625, 1501, 1365, 1227, 1132 cm$^{-1}$; $^1$H NMR (300 MHz, CD$_3$OD) δ 7.86 (d, J=9.3 Hz, 1H), 7.67 (d, J=14.7 Hz, 1H), 7.47 (d, J=14.7 Hz, 1H), 7.34 (dd, J=2.4, 8.4, 1H), 7.33 (m, 1H), 6.72 (d, J=8.1 Hz, 1H), 6.32 (dd, J=8.7, 2.7 Hz, 1H), 6.18 (d, J=2.1 Hz, 1H), 5.24 (t, J=7.2 Hz, 1H), 3.22 (m, 2H), 1.658 (s, 3H), 1.654 (s, 3H); $^{13}$C NMR (75 MHz, CD$_3$OD) δ 193.9, 167.8, 166.7, 159.8, 146.6, 133.7, 132.3, 130.5, 129.5, 128.1, 124.0, 118.2, 116.7, 115.1, 109.5, 104.2, 29.7, 26.4, 18.3, 14.8; $^{13}$C NMR (75 MHz, CDCl$_3$) δ 192.2, 166.0, 163.1, 157.0, 145.1, 135.3, 131.9, 131.0, 128.3, 127.7, 127.3, 121.0, 117.2, 116.2, 114.1, 108.0, 106.4, 103.6, 29.4, 25.7, 17.8; EIMS (m/z, rel intensity) 324 (M$^+$, 46), 268 (8), 188 (20), 175 (100), 137 (77), 69 (34); HRMS m/z calcd. for C$_{20}$H$_{20}$O$_4$ 324.1362; found 324.1357. Anal. Calcd for C$_{20}$H$_{20}$O$_4$.0.25H$_2$O: C, 73.04; H, 6.28 Found: C, 72.77; H, 6.33.

1-(2,4-Dihydroxyphenyl)-3-(4-methoxy-3-(3-methylbut-2-enyl)phenyl)prop-2-en-1-one (7d). The compound was isolated as light yellow solid in 85% yield. $R_f$=0.45 (25% EtOAc-hexanes); mp 166-168° C. IR (KBr) 3306, 2928, 1630, 1601, 1564, 1500, 1370, 1255, 1230, 1141 cm$^{-1}$; $^1$H NMR (300 MHz, (CD$_3$)$_2$CO) δ 9.51 (s, 1H), 8.07 (d, J=8.4 Hz, 1H), 7.78 (m, 4H), 7.02 (d, J=8.4 Hz, 1H), 6.44 (d, J=8.7 Hz, 1H), 6.34 (dd, J=3.0, 16.2 Hz, 1H), 5.30 (t, J=7.2 Hz, 1H), 3.89 (s, 3H), 3.33 (d, J=7.2 Hz, 2H), 1.72 (s, 3H), 1.70 (s, 3H); $^{13}$C NMR (75 MHz, (CD$_3$)$_2$CO) δ 192.5, 167.3, 165.8, 160.4, 145.0, 134.1, 133.0, 132.6, 131.1, 130.6, 129.4, 127.9, 122.9, 118.4, 114.2, 111.3, 108.4, 103.5, 55.7, 25.6, 17.6; negative ESIMS (m/z, rel intensity) 337 (M-H$^+$, 100); positive ESIMS (m/z, rel intensity) 339 (MH$^+$, 79), 322 (100); HRESIMS m/z calcd. for C$_{21}$H$_{23}$O$_4$ 339.1591; found 339.1591.

3-(4-Hydroxy-3-(3-methylbut-2-enyl)phenyl)-1-(2-hydroxy-4-methoxyphenyl)prop-2-en-1-one (7f). The compound was isolated as yellow solid in 89% yield. $R_f$=0.34 (20% EtOAc-hexanes); mp 80-82° C. IR (neat) 3317, 2923, 2852, 1628, 1571, 1504, 1365, 1242, 1154, 1129 cm$^{-1}$; $^1$H NMR (300 MHz, CDCl$_3$) δ 7.83 (d, J=3.9 Hz, 1H), 7.78 (m, 1H), 7.41 (m, 3H), 6.82 (d, J=8.1 Hz, 1H), 6.47 (d, J=2.7 Hz, 1H), 6.44 (brs, 1H), 5.51 (s, 1H), 5.30 (t, J=7.2 Hz, 1H), 3.82 (s, 3H), 3.36 (d, J=6.6 Hz, 2H), 1.775 (s, 3H), 1.772 (s, 3H); $^{13}$C NMR (75 MHz, CDCl$_3$) δ 191.9, 166.5, 165.9, 156.9, 145.8, 144.5, 136.4, 135.7, 131.1, 130.9, 128.3, 127.6, 127.4, 121.0, 117.5, 116.3, 107.6, 109.4, 101.0, 55.5, 29.7, 25.8, 17.9; EIMS (m/z, rel intensity) 338 (M$^+$, 53), 282 (9), 165 (100), 151 (100), 133 (27), 69 (34); HRMS m/z calcd. for C$_{21}$H$_{22}$O$_4$ 338.1518; found 338.1513. Anal. Calcd for C$_{21}$H$_{22}$O$_4$.3.1H$_2$O: C, 63.98; H, 7.21. Found: C, 63.61; H, 7.64.

General procedure D for synthesis of flavanones 8a-8k. Chalcones 7a-7k (0.2 mmol) and sodium acetate (2.0 mmol) were heated in refluxing ethanol (2 mL) for 36-48 h. The mixture was then allowed to cool to room temperature and poured into ice water (10 mL) and extracted with CH$_2$Cl$_2$ (3×10 mL). The combined organic phase was washed with brine, dried over Na$_2$SO$_4$ and then concentrated in vacuo. The residue was column chromatographed eluting with 15-25% ethyl acetate in hexanes to afford flavanones 8a-8k.

7-(Methoxymethoxy)-2-(4-(methoxymethoxy)-3-(3-methylbut-2-enyl)phenyl)-chroman-4-one (8a). The compound was isolated as clear light yellow oil in 45% (isolated), 91% (based on recovered starting material) yield. $R_f$=0.25 (15% EtOAc-hexanes); IR (neat) 2931, 1682, 1608, 1573, 1496, 1447, 1360, 1247, 1153, 1130, 1079, cm$^{-1}$; $^1$H NMR (300 MHz, CDCl$_3$) δ 7.85 (d, J=8.7 Hz, 1H), 7.24 (m, 2H), 7.09 (d, J=8.1 Hz, 1H), 6.68 (m, 2H), 5.39 (dd, J=13.5, 2.7 Hz, 1H), 5.31 (t, J=7.2 Hz, 1H), 5.21 (s, 2H), 5.18 (s, 2H), 3.47 (s, 3H), 3.46 (s, 3H), 3.36 (d, J=7.2 Hz, 2H), 3.03 (dd, J=13.5, 3.3 Hz, 1H), 2.78 (dd, J=16.8, 2.7 Hz), 1.73 (s, 3H), 1.71 (s, 3H); $^{13}$C NMR (75 MHz, CDCl$_3$) δ 191.0, 163.5, 163.3, 155.2, 132.8, 131.6, 131.2, 128.7, 127.7, 125.0, 122.0, 115.6, 113.8, 111.0, 103.6, 94.2, 94.0, 79.8, 56.3, 56.0, 44.1, 28.7, 25.8, 17.8; EIMS (m/z, rel intensity) 412 (M$^+$, 59), 380 (37), 335 (4), 219 (48), 187 (100), 151 (19), 115 (12), 69 (22); HRMS m/z calcd. for C$_{24}$H$_{28}$O$_6$ 412.1886; found 412.1876. Anal. Calcd for C$_{24}$H$_{28}$O$_4$.1.5H$_2$O: C, 65.95; H, 7.11. Found: C, 66.03; H, 6.65.

7-Hydroxy-2-(4-hydroxy-3-(3-methylbut-2-enyl)phenyl)chroman-4-one (Abyssinone II, 8b). The compound was isolated as crystalline bright yellow solid in 55% (isolated), 96% (based on recovered starting material) yield. $R_f$=0.47 (25% EtOAc-hexanes): mp 76-78° C. IR (KBr) 3301, 1927, 1599, 1504, 1367, 1237, 1128, 1028 cm$^{-1}$; δ $^1$H NMR (300 MHz, CD$_3$OD) δ 7.85 (d, J=8.7 Hz, 1H), 7.19 (m, 2H), 6.84 (d, J=8.7 Hz, 1H), 6.56 (dd, J=2.3, 8.7 Hz, 1H), 6.47 (d, J=2.3 Hz, 1H), 5.36 (dd, J=2.8, 13.4 Hz, 1H), 5.31 (t, J=7.2 Hz, 1H), 3.37 (d, J=7.2 Hz, 2H), 3.07 (dd, J=3.7, 13.4 Hz, 1H), 2.79 (dd, J=2.9, 16.9 Hz, 1H), 1.77 (s, 3H), 1.76 (s, 3H); EIMS (m/z, rel intensity) 324 (M$^+$, 53), 307 (15), 255 (10), 189 (6), 175 (100), 137 (87), 69 (49); HRMS m/z calcd. for C$_{20}$H$_{20}$O$_4$ 324.1362; found 324.1353. Anal. Calcd for C$_{20}$H$_{20}$O$_4$.0.6H$_2$O: C, 71.67; H, 6.38. Found: C, 71.51; H, 6.63.

2-(4-Methoxy-3-(3-methylbut-2-enyl)phenyl)-7-(methoxymethoxy)chroman-4-one (8c). The compound was isolated as clear light yellow oil in 45% (isolated), 89% (based on recovered starting material) yield. $R_f$=0.5 (20% EtOAc-hexanes); IR (neat) 2962, 1683, 1610, 1574, 1503, 1446, 1333, 1251, 1154, 1128, 1081 cm$^{-1}$; $^1$H NMR (300 MHz, CDCl$_3$) δ 7.87 (d, J=8.7 Hz, 1H), 7.26 (m, 2H), 6.88 (d, J=8.1 Hz, 1H), 6.89 (m, 2H), 5.39 (dd, J=13.8, 2.7 Hz, 1H), 5.31 (t, J=6.0 Hz, 1H), 5.19 (s, 2H), 3.85 (s, 3H), 3.47 (s, 3H), 3.34 (d, J=6.9 Hz, 2H), 3.06 (dd, J=13.8, 3.3 Hz, 1H), 2.78 (dd, J=14.4, 2.7 Hz), 1.75 (s, 3H), 1.71 (s, 3H); $^{13}$C NMR (75 MHz, CDCl$_3$) δ 191.1, 163.5, 163.3, 157.6, 132.8, 130.5, 130.3, 128.8, 127.4, 125.0, 121.9, 115.5, 110.9, 110.1, 103.5, 93.9, 79.9, 56.3, 55.4, 44.1, 28.4, 25.7, 17.7; EIMS (m/z, rel intensity) 382 (M$^+$, 100), 351 (26), 337 (13), 207 (15), 202 (29), 189 (85), 147 (28), 115 (29), 91 (32), 69 (26), 55(15); HRMS m/z calcd. for C$_{23}$H$_{26}$O$_5$ 382.1780; found 382.1781. Anal. Calcd for C$_{23}$H$_{26}$O$_5$: C, 72.23; H, 6.85. Found: C, 72.11; H, 6.75.

7-Hydroxy-2-(4-methoxy-3-(3-methylbut-2-enyl)phenyl)chroman-4-one (8d). The compound was isolated as light yellow oil in 30% (isolated), 90% (based on recovered starting material) yield. $R_f$=0.44 (25% EtOAc-hexanes); IR (neat) 3218, 2963, 2927, 1660, 1600, 1504, 1463, 1330, 1257, 1157, 1122 cm$^{-1}$; $^1$H NMR (300 MHz, CDCl$_3$) δ 7.83 (d, J=8.7 Hz, 1H), 7.23 (dd, J=8.4, 2.1 Hz, 1H), 7.21 (d, J=2.4 Hz, 1H), 6.85 (d, J=8.4 Hz, 1H), 6.52 (dd, J=7.2, 1.2 Hz, 1H), 6.44 (d, J=2.1 Hz, 1H), 5.35 (dd, J=13.2, 2.7 Hz, 1H), 5.26 (t, J=7.2 Hz, 1H), 3.82 (s, 3H), 3.32 (d, J=7.2 Hz, 2H), 3.06 (dd, J=13.2, 3.9 Hz, 1H), 2.77 (dd, J=17.1, 3.0 Hz), 1.71 (s, 3H), 1.68 (s, 3H); $^{13}$C NMR (75 MHz, CDCl$_3$) δ 190.3, 167.4, 163.9, 157.7, 132.9, 130.6, 130.3, 129.3, 127.5, 125.1, 121.8, 115.8, 118.1, 110.2, 103.4, 79.8, 55.4, 28.4, 25.8, 17.7; EIMS (m/z, rel intensity) 338 (M$^+$, 100), 307 (20), 269 (17), 189 (76), 137 (51), 115 (25), 69 (23); HRMS m/z calcd. for C$_{21}$H$_{22}$O$_4$ 338.1518; found 338.1522. Anal. Calcd for $C_{21}H_{22}O_4 \cdot 3.25H_2O$: C, 63.54; H, 7.78. Found: C, 63.58; H, 7.78.

7-Methoxy-2-(4-(methoxymethoxy)-3-(3-methylbut-2-enyl)phenyl)chroman-4-one (8e). The compound was isolated as clear light yellow oil in 50% (isolated), 97% (based on recovered starting material) yield. $R_f$=0.53 (25% EtOAc-hexanes); IR (neat) 2911, 1686, 1610, 1574, 1503, 1446, 1374, 1332, 1292, 1250, 1154, 1128 cm$^{-1}$; $^1$H NMR (300 MHz, CDCl$_3$) δ 7.84 (d, J=9.3 Hz, 1H), 7.23 (m, 2H), 7.07 (d, J=8.4 Hz, 1H), 6.57 (dd, J=8.7, 2.7 Hz, 1H), 6.44 (d, J=2.4 Hz, 1H), 5.36 (dd, J=13.2, 3.0 Hz, 1H), 5.27 (t, J=7.8 Hz, 1H), 5.20 (s, 2H), 3.80 (s, 3H), 3.45 (s, 3H), 3.34 (d, J=7.2 Hz, 2H), 3.03 (dd, J=13.2, 3.6 Hz, 1H), 2.75 (dd, J=17.1, 3.3 Hz, 1H), 1.70 (s, 3H), 1.69 (s, 3H); $^{13}$C NMR (75 MHz, CDCl$_3$) δ 190.9, 166.1, 163.6, 155.2, 132.8, 131.6, 131.2, 128.7, 127.7, 125.0, 122.0, 114.7, 113.8, 110.1, 100.8, 94.2, 79.9, 55.9, 55.6, 44.1, 28.7, 25.8, 17.8; positive ESIMS (m/z, rel intensity) 383 (MH$^+$, 100), 351 (15), 283 (16), 214 (10), 150 (14); EIHRMS m/z calcd. for $C_{23}H_{26}O_5$ 382.1780; found 382.1778. Anal. Calcd for $C_{23}H_{26}O_5 \cdot 0.25H_2O$: C, 71.38; H, 6.90. Found: C, 71.09; H, 7.38.

2-(4-Hydroxy-3-(3-methylbut-2-enyl)phenyl)-7-methoxychroman-4-one (8f). The compound was isolated as yellow semi solid in 40% (isolated), 88% (based on recovered starting material) yield. $R_f$=0.31 (20% EtOAc-hexanes); IR (neat) 3338, 2924, 1663, 1605, 1573, 1508, 1443, 1364, 1335, 1260, 1159, 1115 cm$^{-1}$; $^1$H NMR (300 MHz, CDCl$_3$) δ 7.84 (m, 1H), 7.37 (m, 2H), 6.84 (m, 1H), 6.57 (dd, J=8.7, 2.1 Hz, 1H), 6.45 (m, 1H), 5.82 (s, 1H), 5.31 (m, 2H), 3.79 (s, 3H), 3.45 (s, 3H), 3.35 (d, J=6.6 Hz, 2H), 3.03 (dd, J=13.8, 3.3 Hz, 1H), 2.76 (dd, J=16.8, 2.7 Hz, 1H), 1.75 (s, 3H), 1.74 (s, 3H); $^{13}$C NMR (75 MHz, CDCl$_3$) δ 191.4, 166.2, 163.7, 154.8, 134.8, 130.5, 128.7, 128.1, 127.5, 125.8, 121.3, 115.8, 114.6, 110.2, 100.8, 79.9, 55.6, 44.0, 29.5, 25.7, 17.8; CIMS (m/z, rel intensity) 339 (MH$^+$, 73), 327 (9), 299 (24), 215 (15), 177 (76), 151 (38), 123 (11); HRMS m/z calcd. for $C_{21}H_{22}O_4$ 338.1518; found 338.1520.

7-Methoxy-2-(4-methoxy-3-(3-methylbut-2-enyl)phenyl)chroman-4-one (8g). The compound was isolated as clear light yellow oil in 56% (isolated), 99% (based on recovered starting material) yield. $R_f$=0.47 (20% EtOAc-hexanes); IR (neat) 3341, 2924, 2851, 1679, 1607, 1499, 1443, 1334, 1254, 1159 cm$^{-1}$; $^1$H NMR (300 MHz, CDCl$_3$) δ 7.83 (d, J=8.7 Hz, 1H), 7.23 (dd, J=8.4, 2.1 Hz, 1H), 7.19 (d, J=2.4 Hz, 1H), 6.85 (d, J=8.1 Hz, 1H), 6.58 (dd, J=8.7, 2.7 Hz, 1H), 6.45 (d, J=2.4 Hz, 1H), 5.37 (dd, J=13.8, 3.0 Hz, 1H), 5.27 (t, J=7.2 Hz, 1H), 3.82 (s, 3H), 3.79 (s, 3H), 3.31 (d, J=7.5 Hz, 2H), 3.03 (dd, J=13.5, 3.3 Hz, 1H), 2.75 (dd, J=17.1, 2.7 Hz), 1.71 (s, 3H), 1.68 (s, 3H); $^{13}$C NMR (75 MHz, CDCl$_3$) δ 190.9, 166.0, 163.6, 157.6, 132.8, 130.5, 130.3, 128.6, 127.5, 125.0, 121.9, 114.7, 110.1, 100.8, 79.9, 55.4, 44.2, 28.4, 25.8, 17.7; EIMS (m/z, rel intensity) 352 (M$^+$, 73), 321 (21), 283 (11), 202 (25), 189 (100), 151 (55), 115 (22), 69 (17); HRMS m/z calcd. for $C_{22}H_{24}O_4$ 352.1675; found 324.1676. Anal. Calcd for $C_{22}H_{24}O_4 \cdot 3.0H_2O$: C, 65.01; H, 7.44. Found: C, 65.22; H, 7.16.

2-(4-Methoxy-3-(3-methylbut-2-enyl)phenyl)chroman-4-one (8h). The compound was isolated as clear light yellow oil in 65% (isolated), 97% (based on recovered starting material) yield. $R_f$=0.49 (15% EtOAc-hexanes); IR (neat) 2975, 1689, 1606, 1577, 1500, 1464, 1305, 1254, 1223, 1148, 1119 cm$^{-1}$; $^1$H NMR (300 MHz, CDCl$_3$) δ 7.92 (d, J=8.7 Hz, 1H), 7.32 (m, 4H), 7.15 (d, J=7.2 Hz, 1H), 6.56 (dd, J=8.7, 2.1 Hz, 1H), 6.49 (s, 1H), 5.39 (dd, J=13.2, 2.7 Hz, 1H), 5.28 (t, J=7.2 Hz, 1H), 5.20 (s, 2H), 3.78 (s, 3H), 3.33 (d, J=7.2 Hz, 2H), 3.01 (dd, J=13.8, 2.7 Hz, 1H), 2.76 (dd, J=16.5, 2.1 Hz, 1H), 1.71 (s, 3H), 1.68 (s, 3H); $^{13}$C NMR (75 MHz, CDCl$_3$) δ 192.4, 161.8, 157.6, 136.0, 132.9, 130.5, 130.2, 127.5, 126.9, 125.0, 121.9, 121.3, 120.8, 118.1, 110.1, 79.5, 55.4, 44.3, 28.4 25.7, 17.7; EIMS (m/z, rel intensity) 322 (M$^+$, 73), 267 (10), 253 (23), 189 (46), 147 (72), 121 (100), 92 (60), 65 (36), 55 (21). Anal. Calcd for $C_{21}H_{22}O_3$: C, 78.23; H, 6.88. Found: C, 78.00; H, 6.87.

7-Methoxy-2-(3-(3-methylbut-2-enyl)phenyl)chroman-4-one (8l). The compound was isolated as clear very light yellow oil in 55% (isolated), 95% (based on recovered starting material) yield. $R_f$=0.48 (15% EtOAc-hexanes); IR (neat) 2923, 1683, 1607, 1574, 1442, 1259, 1158, 1113 cm$^{-1}$; $^1$H NMR (300 MHz, CDCl$_3$) δ 7.82 (d, J=8.7 Hz, 1H), 7.32 (m, 4H), 7.15 (d, J=7.2 Hz, 1H), 6.56 (dd, J=8.7, 2.1 Hz, 1H), 6.49 (s, 1H), 5.39 (dd, J=13.2, 2.7 Hz, 1H), 5.28 (t, J=7.2 Hz, 1H), 5.20 (s, 2H), 3.78 (s, 3H), 3.33 (d, J=7.2 Hz, 2H), 3.01 (dd, J=13.8, 2.7 Hz, 1H), 2.76 (dd, J=16.5, 2.1 Hz, 1H), 1.71 (s, 3H), 1.68 (s, 3H); $^{13}$C NMR (75 MHz, CDCl$_3$) δ 190.6, 166.0, 163.5, 142.5, 138.7, 132.9, 128.8, 128.5, 126.2, 123.5, 122.6, 114.7, 110.1, 100.8, 80.1, 55.6, 44.2, 34.2, 25.7, 16.9; EIMS (m/z, rel intensity) 322 (M$^+$, 88), 253 (29), 177 (100), 151 (77), 122 (55), 107 (53), 69 (71), 55 (73); HRMS m/z calcd for $C_{21}H_{22}O_3$ 322.1569; found 322.1571.

7-Methoxy-2-(4-methoxyphenyl)chroman-4-one (8j). The compound was isolated as clear oil in 65% (isolated), 99% (based on recovered starting material) yield. $R_f$=0.5 (15% EtOAc-hexanes); IR (neat) 3003, 2961, 1680, 1609, 1574, 1515, 1444, 1275, 1257, 1158, 1113 cm$^{-1}$; $^1$H NMR (300 MHz, CDCl$_3$) δ 7.83 (d, J=8.7 Hz, 1H), 7.36 (m, 2H), 6.92 (m, 2H), 6.57 (dd, J=8.7, 2.7 Hz, 1H), 6.44 (d, J=2.4 Hz, 1H), 5.37 (d, J=13.8, 3.3 Hz, 1H), 3.79 (s, 3H), 3.78 (s, 3H), 3.01 (dd, J=13.2, 3.3 Hz, 1H), 2.76 (dd, J=17.1, 3.0 Hz, 1H); $^{13}$C NMR (75 MHz, CDCl$_3$) δ 190.7, 166.0, 163.5, 159.8, 130.7, 128.6, 127.7, 114.7, 114.1, 110.1, 100.8, 79.7, 55.5, 55.3, 44.0; EIMS (m/z, rel intensity) 284 (M$^+$, 80), 269 (7), 177 (13), 134 (100), 121 (53), 108 (9), 91 (24); HRMS m/z calcd. for $C_{17}H_{16}O_4$ 284.1049; found 284.1051. Anal. Calcd for $C_{17}H_{16}O_4$: C, 71.82; H, 5.67. Found: C, 71.52; H, 5.78.

7-Methoxy-2-(4-(3-methylbut-2-enyloxy)phenyl)chroman-4-one (8k). The compound was isolated as solid in 50% (isolated), 88% based on recovered starting material) yield: mp 108-110° C. Rf=0.31 (25% EtOAc-hexanes); IR (neat) 2917, 1723, 1680, 1609, 1513, 1444, 1385, 1257, 1158, 1113 cm 1; $^1$H NMR (300 MHz, CDCl3) □7.83 (d, J=8.7 Hz, 1H), 7.36 (m, 2H), 6.93 (m, 2H), 6.57 (dd, J=8.7, 2.1 Hz, 1H), 6.44 (d, J=2.1 Hz, 1H), 5.46 (m, 1H), 5.37 (dd, J=13.2, 2.7 Hz, 1H), 4.50 (d, J=6.6 Hz, 2H), 3.79 (s, 3H), 3.03 (dd, J=13.8, 3.9 Hz, 1H), 2.76 (dd, J=17.1, 3.3 Hz, 1H), 1.77 (s, 3H), 1.72 (s, 3H); 13C NMR (75 MHz, CDCl3) □ 190.8, 166.1, 163.5, 159.1, 138.4, 130.6, 128.6, 127.6, 119.3, 114.8, 110.1, 100.8, 79.7, 64.7, 55.5, 44.0, 25.8, 18.1; CIMS (m/z, rel intensity) 339 (MH$^+$, 100), 299 (5), 271 (30), 215 (6), 177 (32), 151 (6); HRESIMS m/z calcd. for C21H22O4 338.1518; found 338.1522.

3-Hydroxy-1-(2-hydroxy-4-methoxyphenyl)-3-(4-methoxy-3-(3-methylbut-2-enyl)phenyl)propan-1-one (9). A solution of LiHMDS in THF (1 M, 7.2 mL, 7.2 mmol) was added to a well-stirred solution of acetophenone 6b (500 mg, 3.0 mmol) in THF (15 mL) under argon at −78° C. The reaction mixture was stirred at −78° C. for 1 h and at −10° C. for 2 h and was cooled again to −78° C., and a solution of aldehyde 5b (615 mg, 3.0 mmol) in THF (2 mL) was added in one portion. Stirring was continued at −78° C. for 30 min and then the cooling bath was removed and the reaction mixture was stirred at room temperature. Stirring was continued for 24 h and the reaction mixture was quenched by addition of saturated NH4Cl (10.0 mL). The aqueous layer was extracted with ethyl acetate, washed with brine, dried (Na2SO4), and then concentrated in vacuo. The residue was column chromatographed, eluting with 50% ethyl acetate in hexanes, to afford compound 15 as clear oil (430 mg, 39% yield). Rf=0.27 (50% EtOAc-hexanes); IR (neat) 1631 cm 1; H NMR (500 MHz, CDCl3) □12.67 (s, 1H), 7.65 (d, J=10.0 Hz, 1H), 7.20 (m, 2H), 6.88 (d, J=5.0 Hz, 1H), 6.44 (m, 2H), 5.31 (t, J=2.7 Hz, 1H), 5.28 (dd, J=8.3, 1.2 Hz, 1H), 3.83 (s, 6H), 3.33 (m, 4H), 1.79 (s, 3H), 1.77 (s, 3H); 13C NMR (75 MHz, CDCl3) □203.7, 166.5, 165.6, 157.0, 134.8, 132.6, 131.9, 130.4, 127.0, 124.4, 122.4, 113.7, 110.3, 108.0, 101.0, 70.0, 55.7, 55.6, 46.8, 28.7, 25.9, 17.9; EIMS (m/z, rel intensity) 370 (M+, 1), 352 (5), 321 (1), 218 (10), 203 (12), 189 (9), 135 (12), 108 (15), 91 (32), 69 (100), 43 (60); negative ion ESIMS (m/z, rel intensity) 369 [(M-H)−]; HRMS calcd. for C22H26O5 370.1780, found 370.1783.

3,6-Dihydroxy-2-methoxyacetophenone (10). A solution of 2-hydroxy-6-methoxy-acetophenone (9, 5.0 g, 30.1 mmol) in 10% sodium hydroxide (57.5 g in 575 mL $H_2O$) was added dropwise at room temperature to an aqueous solution of potassium persulfate (8.2 g, 30.3 mmol) in water (350 mL) with stirring for 7 d at 20° C. The mixture was cooled in an ice bath, acidified to pH 5-6 with concd HCl and left overnight at room temperature. The unreacted starting material was removed by extraction with ethyl acetate and the aqueous solution was further acidified to pH 2, and then heated for 4 h on a water bath after addition of solid sodium sulfite (5.8 g, 46.0 mmol). The cooled solution was extracted with chloroform (3×100 mL). The organic extract was evaporated under reduced pressure and the residue was purified by chromatography on silica gel (eluent: $CHCl_3$) to give 3,6-dihydroxy-2-methoxyacetophenone (10) as a pale greenish-yellow solid (3.2 g, 60%): mp 95° C. (lit 94-97° C.). $R_f$=0.25 ($SiO_2$, $CHCl_3$); $^1$H NMR (300 MHz, $CDCl_3$) δ 12.0 (s, 1H), 7.12 (d, J=9.2 Hz, 1H), 6.67 (d, J=9.2 Hz, 1H), 5.08 (s, 1H), 3.81 (s, 3H), 2.70 (s, 3H).

6-Hydroxy-2,3-dimethoxyacetophenone (11). A mixture of 3,6-dihydroxy-2-methoxyacetophenone (10, 1.3 g, 7.1 mmol) and oven-dried potassium carbonate (1.0 g, 7.6 mmol) in dry acetone was stirred for 10 min. Dimethyl sulfate (0.6 mL, 7.1 mmol) was added dropwise to the reaction mixture and the mixture was stirred for 7 d at room temperature. The solvent was evaporated under reduced pressure and water (25 mL) was added to the residue. The mixture was extracted with chloroform (3×100 mL) and the organic phase was dried over $Na_2SO_4$ and evaporated under reduced pressure. The residue was column chromatographed on silica gel eluting with $CHCl_3$ to afford compound II (1.26 g, 89% yield). $R_f$=0.75 ($SiO_2$, $CHCl_3$); $^1$H NMR (300 MHz, $CDCl_3$) δ 7.10 (d, J=9.3 Hz, 1H), 6.66 (d, J=9.3 Hz, 1H), 3.92 (s, 3H), 3.81 (s, 3H), 2.70 (s, 3H).

Zapotin (15). A solution of LiHMDS in THF (1 M, 20 mL, 20 mmol) was added to a well-stirred solution of acetophenone 11 (1.0 g, 5.1 mmol) in THF (10 mL) under argon at −78° C. over 15 min. The reaction mixture was stirred at −78° C. for 1 h and at −10° C. for 2 h and was cooled again to −78° C., and a solution of 2,6-dimethoxybenzoyl chloride 13 (1.38 g, 90% tech. grade, 6.2 mmol) in THF (10 mL) was added in one portion. Stirring was continued at −78° C. for 1 h and at room temperature for 24 h (until the disappearance of the starting material by TLC). The reaction mixture was poured into a mixture of ice (50 g) and concd HCl (5.4 mL) and extracted with $CHCl_3$ (3×100 mL). The solvent was evaporated from the dried ($Na_2SO_4$) extracts and the residue was dried under vacuum for 24 h. A small portion of the crude product was taken out and purified by column chromatography on silica gel (eluent EtOAc-hexanes 3:1) to give compound 14: mp 119-120° C. $R_f$=0.55 ($SiO_2$, EtOAc-hexanes 3:1); IR (neat) 2939, 2838, 1610, 1593, 1574, 1474, 1269, 1254, 1112 cm$^{-1}$; $^1$H NMR (300 MHz, $CDCl_3$) δ 7.30 (t, J=8.7 Hz, 1H), 7.02 (d, J=8.7 Hz, 1H), 6.87 (s, 1H), 6.67 (d, J=8.7 Hz, 1H), 6.58 (d, J=8.4 Hz, 2H), 3.80 (s, 6H), 3.78 (s, 6H); $^{13}$C NMR (75 MHz, $CDCl_3$) δ 193.6, 178.2, 158.0, 155.9, 145.5, 131.5, 120.4, 114.1, 112.7, 105.8, 104.0, 61.5, 57.1, 56.0; EIMS (m/z, relative intensity) 360 (M+, 6), 329 (3), 222 (2), 180 (7), 165 (100), 150 (9), 137 (5), 122 (5), 107 (7); HRMS m/z calcd for ($C_{19}H_2O_7$) 360.1209, found 360.1213. Anal. ($C_{19}H_{22}O_7$) C, H. The rest of the residue was mixed with glacial acetic acid (20.0 mL) and sulfuric acid (0.1 mL) and heated at 95-100° C. under argon atmosphere for 3.5 h. Solvent was removed under reduced pressure and the residue was poured into water (100 mL). The mixture was extracted with chloroform (3×100 mL), dried with $Na_2SO_4$ and the residue was chromatographed with silica gel (eluent ethyl acetate-hexane, 3:1) to yield pure zapotin (15, 1.4 g, 82%): mp 146-147° C. (lit 147-148° C.). $R_f$=0.25 ($SiO_2$, EtOAc-hexane 3:1); IR (neat) 2939, 2840, 1650, 1592, 1475, 1417, 1357, 1281, 1255, 1111 cm$^{-1}$; $^1$H NMR (300 MHz, $CDCl_3$) δ 7.35 (t, J=8.7 Hz, 1H), 7.25 (d, J=9.3 Hz, 1H), 7.16 (d, J=9.3 Hz, 1H), 6.59 (d, J=8.4 Hz, 2H), 6.26 (s, 1H), 3.94 (s, 3H), 3.88 (s, 3H), 3.75 (s, 6H); $^{13}$C NMR (75 MHz, $CDCl_3$) δ 177.9, 158.7, 158.2, 152.2, 149.3, 147.4, 131.8, 119.0, 118.5, 114.9, 113.5, 110.9, 103.6, 61.5, 56.8, 55.7; EIMS (m/z, relative intensity) 342 (M+, 50), 327 (100), 311 (7), 283 (5), 253 (8), 237 (3), 197 (3), 182 (5), 165 (37), 137 (83), 109 (26), 91 (18), 69 (19), 53 (14); HRMS m/z calcd for ($C_{19}H_{18}O_6$) 342.1103, found 342.1107. Anal. ($C_{19}H_{18}O_6$) C, H.

METHOD EXAMPLES

Assay for inhibition of aromatase activity. The synthetic (±)-abyssinone II and (±)-analogues (compounds 8a-8k), as well as the respective chalcone (enone) precursors (compounds 7a-7k), were tested for aromatase inhibition. Aromatase inhibition is quantified by measuring the fluorescent intensity of fluorescein, the hydrolysis product of dibenzylfluorescein by aromatase. In brief, the test substance (10 μL) is pre-incubated with the NADPH regenerating system (90 μL of 2.6 mM NADP+, 7.6 mM glucose 6-phosphate, 0.8 U/mL glucose-6-phosphate dehydrogenase, 13.9 mM $MgCl_2$, and 1 mg/mL albumin in 10 mL of 50 mM potassium phosphate, pH 7.4) for 10 min at 37° C. before 100 μL of the enzyme and substrate mixture [800 μL enzyme (CYP19, BD Biosciences, San Jose, Calif.), 0.4 μM dibenzylfluorescein and 4 mg/mL albumin in 10 mL of 50 mM potassium phosphate, pH 7.4] are added. Then, the reaction mixture is incubated for 30 min at 37° C. to allow aromatase to generate the product, and quenched with 75 μL 2 N NaOH. After the reaction is terminated, a 5-min shaking followed by a 2-h incubation at 37° C. enhances the noise/background ratio and fluorescence is measured at 485 nm (excitation) and 530 nm (emission). All experiments were performed in duplicate and the average was used for calculation of $IC_{50}$ values (Table 2). Compounds were tested in comparison to aminogluthethimide used as positive control.

TABLE 2
Aromatase inhibition by chalcone (7) and flavanone (8) compounds
| Entry No. | Chalcone (7) | IC$_{50}$ (μM) |
|---|---|---|
| a. | 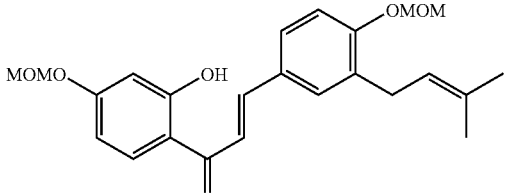 | >242.5 |
| b. | 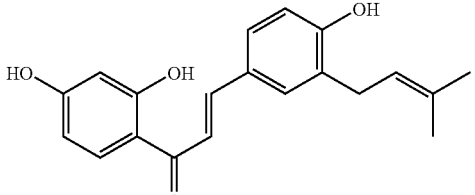 | >308.3 |
| c. | 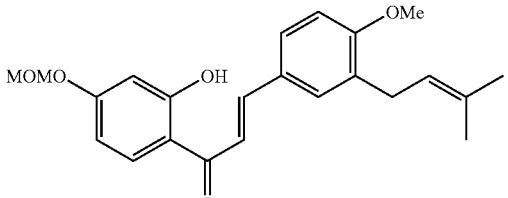 | >261.5 |
| d. | 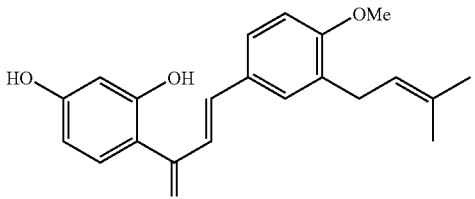 | 82.94 ± 44.27 |
| e. | 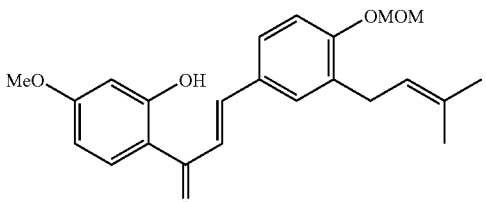 | >261.5 |
| f. | 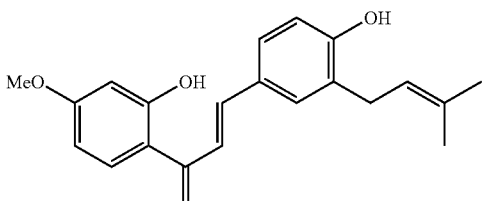 | >295.5 |
| g. | 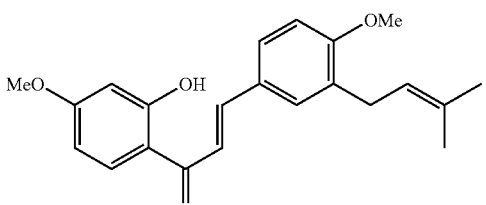 | >283.75 |

TABLE 2-continued
Aromatase inhibition by chalcone (7) and flavanone (8) compounds
| | | |
|---|---|---|
| h. | 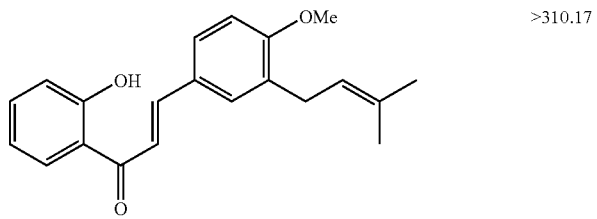 | >310.17 |
| i. | 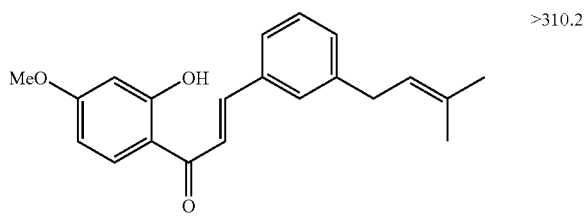 | >310.2 |
| j. | 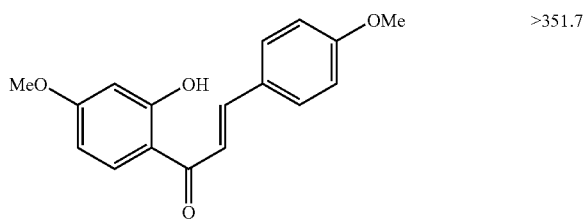 | >351.7 |
| k. | 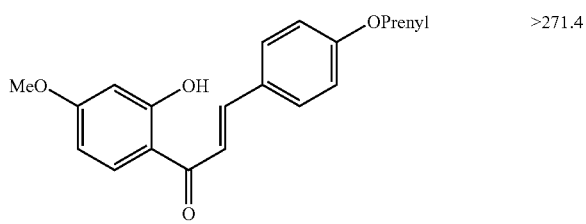 | >271.4 |
| | 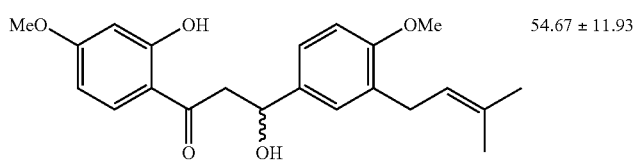 | 54.67 ± 11.93 |
| | 9 | |
| Entry No. | Flavanone (8) | IC$_{50}$ (µM) |
|---|---|---|
| a. | 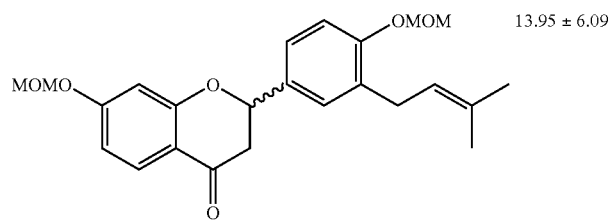 | 13.95 ± 6.09 |

TABLE 2-continued

Aromatase inhibition by chalcone (7) and flavanone (8) compounds

| | | |
|---|---|---|
| b. | [structure: 7-OH flavanone with 4'-OH, 3'-prenyl] | 40.95 ± 11.31 |
| c. | [structure: 7-OMOM flavanone with 4'-OMe, 3'-prenyl] | 7.67 ± 3.27 |
| d. | [structure: 7-OH flavanone with 4'-OMe, 3'-prenyl] | 4.08 ± 2.10 |
| e. | [structure: 7-OMe flavanone with 4'-OMOM, 3'-prenyl] | 25.14 ± 6.38 |
| f. | [structure: 7-OMe flavanone with 4'-OH, 3'-prenyl] | 4.75 ± 0.61 |
| g. | [structure: 7-OMe flavanone with 4'-OMe, 3'-prenyl] | 3.67 ± 1.61 |
| h. | [structure: flavanone with 4'-OMe, 3'-prenyl] | 12.10 ± 3.24 |

TABLE 2-continued

Aromatase inhibition by chalcone (7) and flavanone (8) compounds

| | | |
|---|---|---|
| i. | 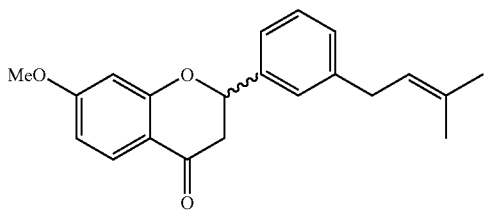 [SMILES: COc1ccc2c(c1)OC(c1cccc(CC=C(C)C)c1)CC2=O] | 4.67 ± 2.15 |
| j. | 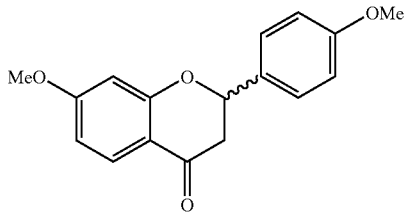 [SMILES: COc1ccc(C2CC(=O)c3ccc(OC)cc3O2)cc1] | 1.86 ± 0.37 |
| k. | 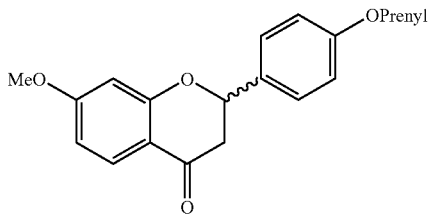 | 28.65 ± 7.96 |

Cell Culture. T24 and HL-60 cells were obtained from the American Type Culture Collection (Rockville, Md.). T24 cells were cultured in MEM medium (Invitrogen, Carlsbad, Calif.) containing 10% heat-inactivated fetal bovine serum, non-essential amino acids, 1 mM sodium pyruvate (BioWhittaker, Walkersville, Md.), 100 units of penicillin/mL, 100 μg streptomycin/mL and 250 ng amphotericin B/mL (Gibco Invitrogen, Grand Island, N.Y.). The HL-60 cell line was maintained in suspension culture using RPMI 1640 medium (Invitrogen) supplemented with 10% heat-inactivated fetal bovine serum, 100 units of penicillin/mL and 100 μg of streptomycin/mL. HepG2 human hepatoma cells stably transfected with NF-κB-luciferase plasmid were maintained in Ham's F12 supplemented with 10% heat-inactivated fetal bovine serum, 100 units/mL penicillin G sodium, 100 μg/mL streptomycin sulfate, 1% MEM amino acid and 0.1% insulin. See, Pezzuto, J. M.; Kosmeder, J.; Park, E. J.; Lee, S. K.; Cuendet, M.; Gills, J. J.; Bhat, K.; Grubjesic, S.; Park, H. S.; Mata-Greenwood, E.; Tan, Y.; Yu, R.; Lantvit, D. D.; Kinghorn, A. D., *Characterization of Natural Product Chemopreventive Agents*. Humana Press, Inc.: Totowa, N.J., 2005; Vol. 2, p 3-37, the disclosure of which is incorporated herein by reference. The cell lines were maintained in a 5% $CO_2$ atmosphere at 37° C. and were routinely tested for mycoplasma contamination.

Inhibition of TPA-Induced Ornithine Decarboxylase (ODC) Activity in T24. Cells. T24 cells were treated with various concentrations of zapotin (15) and determination of ODC activity was performed as follows. See, Gerhauser, C.; Mar, W.; Lee, S. K.; Suh, N.; Luo, Y.; Kosmeder, J.; Luyengi, L.; Fong, H. H. S.; Kinghorn, A. D.; Moriarty, R. M.; Mehta, R. G.; Constantinou, A.; Moon, R. C.; Pezzuto, J. M. Rotenoids Mediate Potent Cancer Chemopreventive Activity through Transcriptional Regulation of Ornithine Decarboxylase. *Nature Med.* 1995, 1, 598-598, the disclosure of which is incorporated herein by reference. In brief, cells were plated at an initial density of $2 \times 10^5$ cells per well in 24-well plates. After an 18 h pre-incubation, a solution of zapotin (15) in DMSO was added in duplicate (5 μL, 0.5% final concentration) before the induction of ODC activity with TPA (200 nM final concentration). After an additional 6 h incubation, plates were washed twice with PBS and kept at −85° C. until tested. ODC activity was directly assayed by measuring the release of $[^{14}C]CO_2$ from L-$[1-^{14}C]$-ornithine HCl in the presence of 190 μM nonradioactive ornithine HCl. The amount of radioactivity captured in NaOH-impregnated filter discs was determined by scintillation counting in 24-well plates using a Wallac 1450 Microbeta liquid scintillation counter. Protein was determined according to the Lowry procedure. Interfering dithiothreitol contained in the reaction mixture was destroyed by adding chloramine T (50 μL, 8 mg/mL) to each well (30 min incubation at RT), followed by NaOH (50 μM, 5.7 M) to solubilize the protein. The protein was measured in 96-well plates using an aliquot of the reaction mixture and bovine serum albumin as a standard. The optical density was measured at 660 nm using a BT2000 Microkinetic Reader. The results were calculated as nmol $[^{14}C]CO_2$/h/mg protein and expressed as a percentage in comparison with a control treated with DMSO and TPA (12-O-tetradecanoylphorbol-13-acetate). Dose-response curves were prepared and the results were expressed as $IC_{50}$ values in micromolar concentrations. $IC_{50}$ values were generated from the results of four serial dilutions of zapotin (15) tested in duplicate. Zapotin was found to be active, with an $IC_{50}$ of 1.9 μM. Standard inhibitors of TPA-induced ODC activity tested in the same system include apigenin ($IC_{50}$ 6.0 μM), menadione ($IC_{50}$ 8.3 μM), and deguelin ($IC_{50}$ 0.1 μM).

Inhibition of TPA-Induced NF-κB Activity in HepG2 Cells. HepG2 cells stably transfected with NF-κB-luciferase plasmid were treated with various concentrations of zapotin

(15) and determination of luciferase activity was performed as follows. See, Homhual, S.; Zhang, H. J.; Bunyapraphatsara, N.; Kondratyuk, T. P.; Santarsiero, B. D.; Mesecar, A. D.; Herunsalee, A.; Chaukul, W.; Pezzuto, J. M.; Fong, H. H. S. Bruguiesulfurol, a New Sulfur Compound from *Bruguiera gymnorrhiza. Planta Med.* 2006, 72, 255-260, the disclosure of which is incorporated herein by reference. In brief, transfected cells were incubated for 48 h in 96-well plates. After 6 h incubation with TPA (100 nM) and zapotin (15), cells were analyzed for luciferase activity. Cells were washed with PBS, lysed using 50 µL 1× Reporter Lysis Buffer (Promega, Madison, Wis.) for 10 min, and the luciferase determination was performed according to the manufacturer's protocol. Data were expressed as the concentration required to inhibit activation by 50% ($IC_{50}$ value). Tumor necrosis factor (TNF)-α was used as a standard inhibitor ($IC_{50}$ 15-25 ng/mL). $IC_{50}$ values were generated from the results of four serial dilutions of zapotin (15) tested in duplicate. With the experimental conditions used, no signs of overt cellular toxicity were observed. Zapotin was found to inhibit TPA-induced NF-κB activity in HepG2 cells stably transfected with NF-κB-luciferase plasmid with an $IC_{50}$ value of 16.4 µM.

Induction of Differentiation by Zapotin in HL-60 Cell Line. HL-60 cells were tested using a 4-day protocol. See, Suh, N.; Luyengi, L.; Fong, H. H. S.; Kinghorn, A. D.; Pezzuto, J. M. Discovery of Natural Product Chemopreventive Agents Utilizing HL-60 Cell Differentiation as a Model. *Anticancer Res.* 1995, 15, 233-240, the disclosure of which is incorporated herein by reference. In brief, cells in log phase (approximately $10^6$ cells/mL) were diluted to $10^5$ cells/mL and preincubated overnight (18 h) in 24-well plates to allow cell growth recovery. Then, samples dissolved in DMSO were added, keeping the final DMSO concentration at 0.1% (v/v). Control cultures were treated with the same concentration of DMSO. After four days of incubation, cells were analyzed to determine the percentage exhibiting functional nitroblue tetrazolium (NBT) reduction, and cell surface markers of differentiated cells.

Evaluation of NBT reduction was used to assess the ability of sample-treated cells to produce superoxide when challenged with TPA. A 1:1 (v/v) mixture of a cell suspension ($10^6$ cells) and TPA/NBT solution [2 mg/mL NBT and 1 µg/mL TPA in phosphate buffer saline (PBS)] was incubated for 1 h at 37° C. Then, cells were smeared on glass slides, and counterstained with 0.3% (w/v) safranin O in methanol. Positive cells reduce NBT yielding intracellular black-blue formazan deposits and were quantified by microscopic examination of >200 cells. Results were expressed as a percentage of positive cells.

Cells ($10^6$), prewashed with PBS, were resuspended in 100 µL diluent (PBS with 0.1% sodium azide and 1% BSA) and incubated for 30 min at room temperature with the monoclonal antibodies anti-CD-11b (Sigma, St. Louis, Mo.), anti-CD13 (Caltag, Burlingame, Calif.), anti-CD14 (Sigma), and anti-CD15 (Caltag), conjugated with FITC. Cells were washed with 20 volumes of diluent, and resuspended in 0.5 mL of 2% paraformaldehyde for flow cytometry evaluation. Identical samples were prepared using isotype antibodies to correct fluorescence due to non-specific binding.

Zapotin (15) induced 50% of the cells to differentiate at 0.2 µg/mL ($ED_{50}$ 0.5 µM), compared to 10 µM required by apigenin and 30 µM by genistein to exert the same activity, representing a 20-60 fold increase in potency. In the current study, cells were treated with various concentrations of zapotin (15) for 24, 48, 72, or 96 h and harvested after 4 days for evaluation of enzymatic and cell membrane markers of differentiation.

Figure 1:
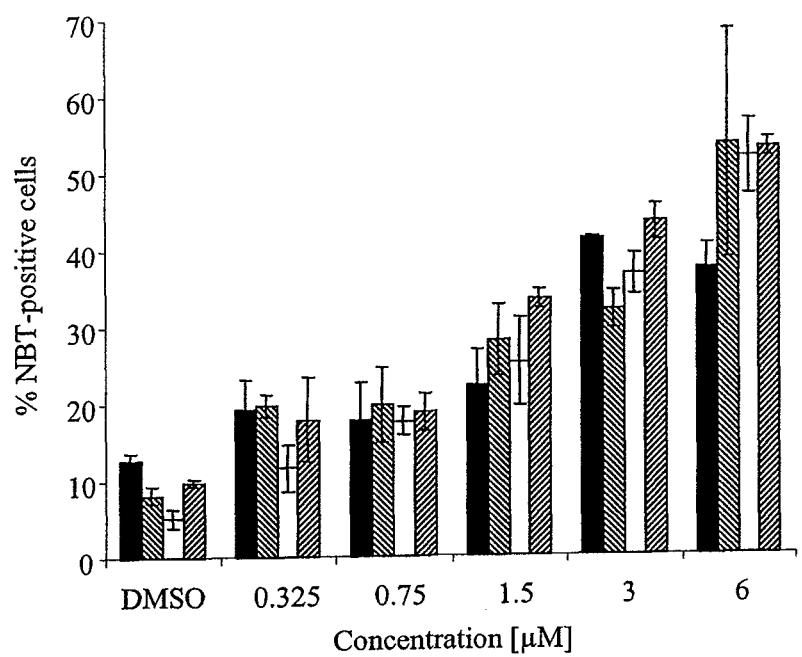
FIG. 1. Commitment toward differentiation of HL-60 cells is obtained at 24 h of exposure to zapotin (15). In each case, total incubation time was 4 days (96 h), and then cells were analyzed for differentiation marker. Cells were treated with the specified concentrations of zapotin (15), which was withdrawn after 24 (■), 48 ((▨),), 72 (□) or 96 ((▧)) h. For the 24, 48, and 72 h exposures, cells were resuspended in fresh complete media for the remaining time. Results are shown as the mean of duplicate samples.

Analysis of NBT (nitroblue tetrazolium)-reduction for evaluation of superoxide formation demonstrated myeloid maturation in HL-60 cells. The irreversibility of zapotin (15) effects on growth and differentiation of HL-60 cells was tested using withdrawal assays during a 4-day experiment. Withdrawal of zapotin (15) after 24 h of exposure resulted in the differentiation of a similar percentage of cells as without withdrawal (FIG. 1), while maintaining a higher cellular viability and density.

Figure 2:
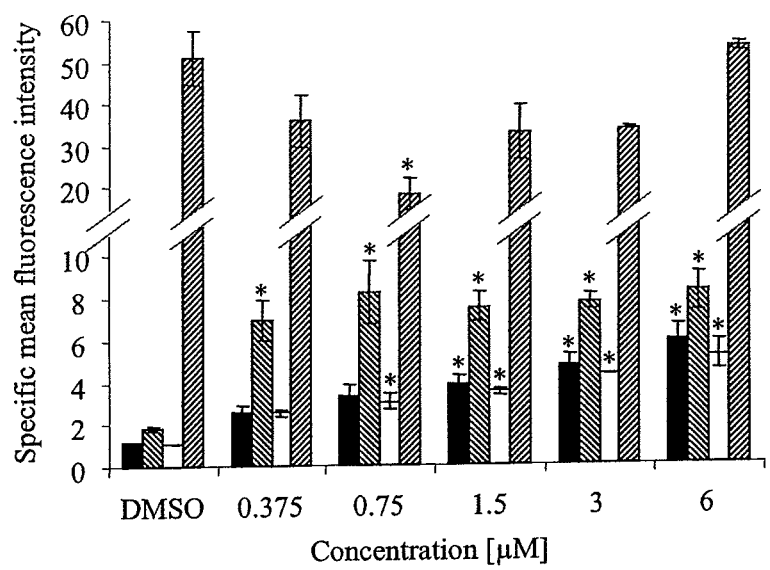
FIG. 2. Effect of zapotin (15) on the membrane phenotype of HL-60 cells. As described herein, cells were induced to differentiate with the indicated concentrations of zapotin (15) using a 4-day protocol, and then analyzed for the following membrane markers of differentiation: CD11b (■), CD13 ((▨),), CD14 (□), and CD15 ((▧)). Results are expressed as the specific mean fluorescence intensity (ratio of antigen antibody fluorescence over isotype antibody fluorescence), and represent the mean of two independent studies. The * indicates a significant difference from control values (p<0.05).

Membrane phenotype was also analyzed using flow cytometry with a set of four myeloid markers (CD11b, CD13, CD14 and CD15). Zapotin (15) up-regulated CD11b, CD13 and CD14, and down-regulated CD15 in HL-60 cells (FIG. 2). Thus, zapotin (15) induced a pattern of expression similar to that produced by macrophage inducers, with down-regulation of CD15 (granulocytic marker) and up-regulation of CD13 and CD11b (granulocytic/monocytic markers). See, Trayner, I. D.; Bustorff, T.; Etches, A. E.; Mufti, G. J.; Foss, Y.; Farzaneh, F., Changes, in Antigen Expression on Differentiating HL-60 Cells treated with Dimethylsulfoxide, all-trans Retinoic Acid, 1α,25-Dihydroxyvitamin $D_3$ or 12-O-Tetradecanoyl phorbol 13-acetate. *Leuk. Res.* 1998, 22, 537-547, the disclosure of which is incorporated herein by reference.

Figure 3:
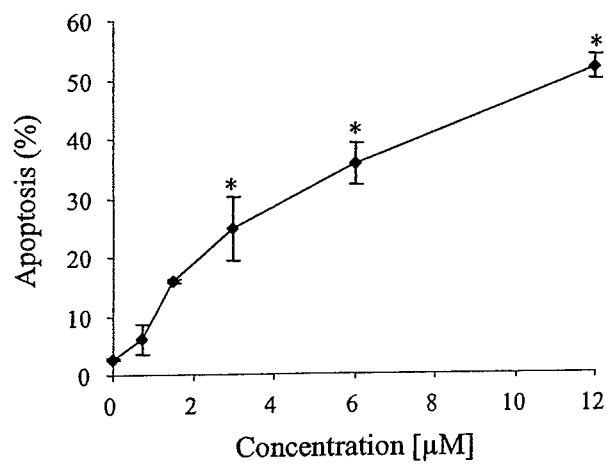
FIG. 3. Dose-dependent induction of apoptosis in HL-60 cells treated with zapotin (15). Cells were treated with the indicated concentrations for 24 h. Apoptosis was quantified by counting nuclei stained with 4',6-diamidino-2-phenylindole (DAPI). Results represent the mean of two independent studies. The * indicates a significant difference from control values (p<0.01).

Induction of Apoptosis by Zapotin in HL-60 Cell Line. Cells were treated with various concentrations of zapotin (15) for 24 h, or with 12 µM zapotin (15) for various time intervals, washed with PBS, and fixed with methanol-acetic acid 1:1 for 30 min at room temperature. Cells were then treated with 4',6-diamidino-2-phenylindole (DAPI, 1 µg/mL) for 15 min at room temperature. DAPI staining of the nucleus was observed by fluorescence microscopy. At least 100 cells were counted for each sample. Dose-response curves showing the percentage of apoptosis at different doses and times were constructed. After a 24 h treatment period, zapotin (15) induced dose-dependent increases in apoptosis, as judged by the formation of apoptotic bodies observed with DAPI staining (FIG. 3), which were significant with doses of 3 µM and higher ($p<0.01$). A time-dependent increase of apoptosis was also observed when cells were treated with 12 µM zapotin (15).

Cell Cycle Analysis. Cells ($3\times10^6$) were treated with various concentrations of zapotin (15) for 24 h, and washed with PBS. Cells were resuspended in 1 mL PBS+9 mL ice-cold 70% EtOH and stored at −20° C. Just before analysis, samples were centrifuged and cell pellets were resuspended in 2 mL of propidium iodide solution (2 µg/mL propidium iodide, 100 µg/mL ribonuclease A in PBS). Solutions were incubated at 37° C. for 1 h, placed on ice and analyzed by flow cytometry. At least 10,000 cells were counted for each sample. The percentage of apoptotic cells was calculated by measuring the area under the subdiploid (DNA<2 N) peak in the plot of cell number against cellular DNA content.

Alternatively, cells were exposed to 5-bromo-2-deoxyuridine (BrdU) for 30 min prior to trypsinization to specifically label S-phase cells. After fixation, cells were stained with fluorescein-conjugated antibody to BrdU and counter stained with propidium iodide following the manufacturer's protocol (Phoenix Flow Systems, San Diego, Calif.). Cell suspensions were analyzed by flow cytometry, and data were collected using appropriate electronic gating to remove background debris and aggregates.

Figure 4:
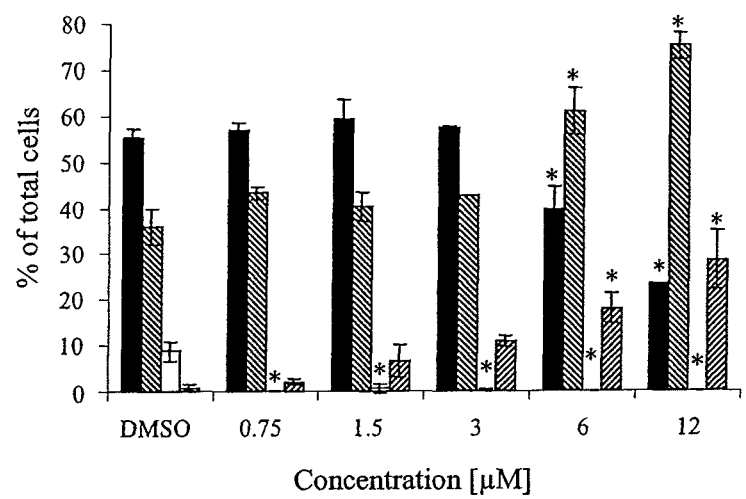
FIG. 4. Cell cycle effects of zapotin (15) in HL-60 cells. Cells were treated with the indicated concentrations for 24 h, fixed in ethanol and stained with PI (propidium iodide) for flow cytometric analysis, as described herein. Values are expressed as percentage of total cells and represent the mean±SD of three determinations, for the following compartments of the cell cycle: $G_1$ (■), S ((▨),), $G_2$/M (□) and apoptotic peak sub $G_1$ ((▧)). The * indicates a significant difference from control values (p<0.01).

Zapotin (15) arrested the cells in the S phase of the cell cycle in a dose-dependent manner (FIG. 4). In the cells treated with 3 µM zapotin (15), 61% of the cells were in S-phase as compared with 36% in the control population. A complete suppression of cells in the $G_2/M$ phase of the cycle could be noted with concentrations of zapotin (15) as low as 0.75 µM.

Also, a dose-dependent increase of the sub $G_1$ peak, characteristic of apoptosis, was evident.

Figure 5:
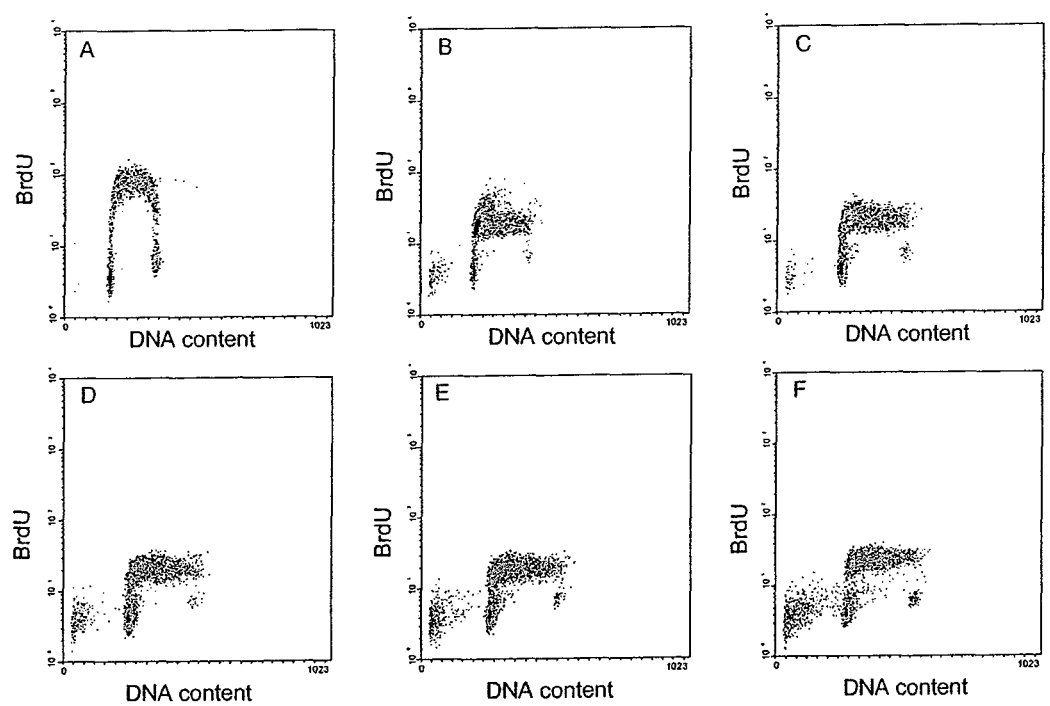
FIG. 5. Effects of zapotin (15) on BrdU incorporation in HL-60 cells.

The effect of zapotin (15) on BrdU incorporation in HL-60 cells is shown in FIG. 5.

Effect of Zapotin on the TPA-Dependent Two-Stage Mouse Skin Carcinogenesis Model. Zapotin given prior to DMBA treatment, using an anti-initiation protocol failed to influence the percentage of tumor bearing mice and the tumor multiplicity. However, the highest dose tested, 10 μM, showed a trend toward lower tumor multiplicity. Zapotin administered during the promotion phase caused decreases in both the percent of mice with tumors and in tumor multiplicity. Zapotin administered during both the initiation and promotion phases had essentially the same effect as zapotin administered during the promotion phase only on the percentage of tumor bearing mice, but the tumor multiplicity was unaffected. At the end of the study, survival was 100% in all the groups, and no animals lost body weight. Results from the in vivo study are presented in the following tables and figures. See FIGS. 6-11.

Statistical analysis. Data were expressed as means±SD and analyzed through one-way analysis of variance (ANOVA), followed by pairwise comparisons made with Dunnett's test, using the SAS statistical package (SAS Institute, Cary, N.C.). All of the tests were two-sided, and, unless otherwise specified, a p value of less than 0.01 was considered to be significant.

The invention claimed is:

1. A compound of the formula

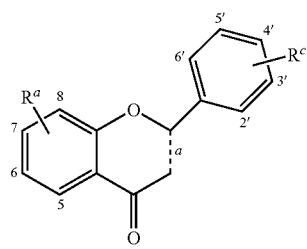

and pharmaceutically acceptable salts thereof, wherein:
bond a is a single bond;
$R^a$ represents 2-4 substituents where at least 2 of said substituents are adjacent substituents and are taken together to form alkylenedioxy, and where any remaining substituents are each independently selected from the group consisting of halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof; and
$R^c$ represents 1-4 substituents each of which is independently selected from the group consisting of halo, hydroxy, optionally substituted alkyl, optionally substituted alkenyl, optionally substituted alkoxy, cyano, nitro, optionally substituted alkylthio, optionally substituted alkylsulfonyl; carboxylic acid and derivatives thereof, and sulfonic acid and derivatives thereof;
provided that at least one of $R^c$ is alkenyl; and
provided that when $R^a$ is 7-hydroxy and alkylenedioxy or 7-alkoxy and alkylenedioxy, $R^c$ is not 4'-hydroxy or 4'-alkoxy.

2. The compound of claim 1 wherein $R^a$ represents 2 adjacent substituents taken together to form alkylenedioxy.

3. The compound of claim 2 wherein $R^c$ includes one or more (3-methylbut-2-enyl) groups.

4. A pharmaceutical composition for treating a patient in need of relief from breast cancer, the composition comprising:
(a) the compound of claim 1; and
(b) one or more pharmaceutically acceptable carriers, diluents, and excipients therefor;
where the compound is present in an amount effective for treating the patient.

5. The composition of claim 4 wherein $R^a$ includes one or more alkoxy groups.

6. The composition of claim 5 wherein $R^c$ also includes one or more alkoxy groups.

7. The composition of claim 6 wherein $R^c$ includes one or more (3-methylbut-2-enyl) groups.

8. A process for preparing a compound of the formula

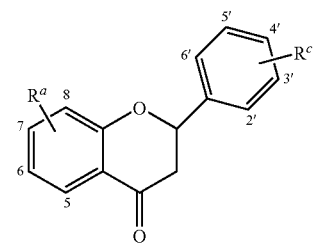

from an enone intermediate, the process comprising: reacting a compound of the formula

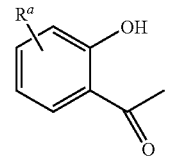

with a compound of the formula

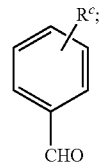

and
cyclizing the enone intermediate, wherein:
$R^a$ represents 2-4 substituents where at least 2 of said substituents are adjacent substituents and are taken together with the attached carbons to form alkylenedioxy, and where any remaining substituents are each independently selected from the group consisting of halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof; and
group consisting of halo, hydroxy, optionally substituted alkyl, optionally substituted alkenyl, optionally substituted alkoxy, cyano, nitro, optionally substituted alkylthio, optionally substituted alkylsulfonyl, carboxylic acid and derivatives thereof, and sulfonic acid and derivatives thereof;
provided that at least one of $R^c$ is alkenyl; and
provided that when $R^a$ is 7-hydroxy and alkylenedioxy or 7-alkoxy and alkylenedioxy, $R^c$ is not-4'-hydroxy or 4'-alkoxy.

9. The process of claim 8 wherein the reacting step is conducted under Claisen-Schmidt conditions and the cyclizing step includes sodium acetate.

10. The process of claim 8 wherein the enone intermediate is of the formula

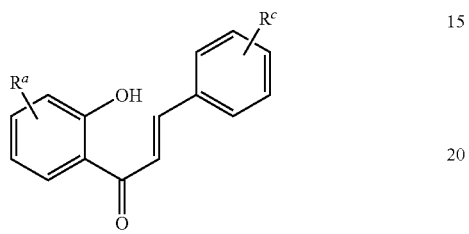

wherein $R^a$ and $R^c$ are as defined in claim 8.

* * * * *